US011455834B2

(12) United States Patent
Mettler May

(10) Patent No.: US 11,455,834 B2
(45) Date of Patent: *Sep. 27, 2022

(54) CODIFICATION AND CUEING SYSTEM FOR SPORT AND VOCATIONAL ACTIVITIES

(71) Applicant: ICUEMOTION LLC, San Francisco, CA (US)

(72) Inventor: Bérénice Mettler May, San Francisco, CA (US)

(73) Assignee: ICUEMOTION LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/889,708

(22) Filed: Jun. 1, 2020

(65) Prior Publication Data
US 2020/0289907 A1    Sep. 17, 2020

Related U.S. Application Data

(63) Continuation of application No. 15/502,612, filed as application No. PCT/US2015/044620 on Aug. 11, 2015, now Pat. No. 10,668,353.
(Continued)

(51) Int. Cl.
*A63F 13/00*    (2014.01)
*G06V 40/20*    (2022.01)
(Continued)

(52) U.S. Cl.
CPC .............. *G06V 40/20* (2022.01); *A63B 69/38* (2013.01); *A63B 71/06* (2013.01); *G06V 40/23* (2022.01); *G16H 20/30* (2018.01)

(58) Field of Classification Search
CPC ..................... A63B 24/0003; A63B 2024/0068
See application file for complete search history.

(56) References Cited

U.S. PATENT DOCUMENTS 4,257,594 A    3/1981   Conrey et al.
4,303,241 A    12/1981  Burroughs
(Continued)

FOREIGN PATENT DOCUMENTS

CN    104107134 A    10/2014
CN    104225890 A    12/2014
(Continued)

OTHER PUBLICATIONS

First Office Action dated Jun. 3, 2021 in connection with Chinese patent application No. 2018800486618, 20 pages including English translation.
(Continued)

*Primary Examiner* — David L Lewis
*Assistant Examiner* — Eric M Thomas
(74) *Attorney, Agent, or Firm* — Dorsey & Whitney LLP

(57) ABSTRACT

A cueing device or system includes one or more sensors configured to take measurement data for one or more participants in an activity. A processor in communication with the sensors analyzes the measurement data to detect events associated with the environment and participants, extracts attributes associated with the events from the measurement data, predicts a movement outcome associated with one of the events based on the attributes, and generates one or more instructions based on the predicted movement outcome. A cue administrator generates one or more anticipatory cues based on the instructions generated by the processor. The cues are administered as cue stimuli encoding timing and magnitude information selected to reduce response time for recognition of the event.

24 Claims, 10 Drawing Sheets

Related U.S. Application Data

(60) Provisional application No. 62/035,569, filed on Aug. 11, 2014.

(51) Int. Cl.
   *A63B 69/38* (2006.01)
   *A63B 71/06* (2006.01)
   *G16H 20/30* (2018.01)

(56) References Cited

U.S. PATENT DOCUMENTS

| | | |
|---|---|---|
| 4,508,510 A | 4/1985 | Clifford |
| 5,031,909 A | 7/1991 | Pecker |
| 5,154,427 A | 10/1992 | Harlan et al. |
| 5,226,650 A | 7/1993 | Suttner |
| 5,368,042 A | 11/1994 | Oneal et al. |
| 5,419,562 A | 5/1995 | Cromarty |
| 5,610,590 A | 3/1997 | Johnson et al. |
| 5,646,911 A | 7/1997 | Davis |
| 5,694,340 A | 12/1997 | Kim |
| 6,032,530 A | 3/2000 | Hock |
| 6,219,032 B1 | 4/2001 | Rosenberg et al. |
| 6,224,493 B1 | 5/2001 | Lee et al. |
| 6,314,339 B1 | 11/2001 | Rastegar et al. |
| 6,565,449 B2 | 5/2003 | Buhler |
| 6,649,905 B2 | 11/2003 | Grenlund |
| 6,659,905 B2 | 12/2003 | Usoro et al. |
| 7,021,140 B2 | 4/2006 | Perkins |
| 7,160,200 B2 | 1/2007 | Grober |
| 7,264,554 B2 | 9/2007 | Bentley |
| 7,536,033 B2 | 5/2009 | Kirby |
| 7,602,301 B1 | 10/2009 | Stirling et al. |
| 7,891,666 B2 | 2/2011 | Kuenzler et al. |
| 8,282,487 B2 | 10/2012 | Wilson et al. |
| 8,323,107 B2 | 12/2012 | Amit |
| 8,337,335 B2 | 12/2012 | Dugan |
| 8,360,904 B2 | 1/2013 | Oleson et al. |
| 8,556,267 B2 | 10/2013 | Gobush |
| 8,589,114 B2 | 11/2013 | Papadourakis |
| 8,602,922 B2 | 12/2013 | Schwenger et al. |
| 8,622,795 B2 | 1/2014 | Edis et al. |
| 8,831,905 B2 | 9/2014 | Papadourakis |
| 8,903,521 B2 | 12/2014 | Goree et al. |
| 8,905,855 B2 | 12/2014 | Fitzpatrick et al. |
| 8,941,723 B2 | 1/2015 | Bentley et al. |
| 8,944,928 B2 | 2/2015 | Kaps et al. |
| 8,944,940 B2 | 2/2015 | Mettler |
| 8,956,238 B2 | 2/2015 | Boyd et al. |
| 8,989,441 B2 | 3/2015 | Han et al. |
| 8,994,826 B2 | 3/2015 | Bentley |
| 9,039,527 B2 | 5/2015 | Bentley et al. |
| 9,656,122 B2 | 5/2017 | Papadourakis |
| 9,694,267 B1 | 7/2017 | Thornbrue et al. |
| 9,901,776 B2 | 2/2018 | Mettler |
| 10,668,353 B2 | 6/2020 | Mettler May |
| 10,854,104 B2 | 12/2020 | Mettler May |
| 2001/0049890 A1* | 12/2001 | Hirsch ............... A43B 17/00 36/132 |
| 2002/0077189 A1 | 6/2002 | Tuer et al. |
| 2002/0107077 A1 | 8/2002 | Buhler |
| 2002/0134153 A1 | 9/2002 | Grenlund |
| 2003/0024311 A1 | 2/2003 | Perkins |
| 2004/0243261 A1 | 12/2004 | King |
| 2004/0259651 A1 | 12/2004 | Storek |
| 2005/0017454 A1 | 1/2005 | Endo et al. |
| 2005/0054457 A1 | 3/2005 | Eyestone et al. |
| 2005/0196737 A1 | 9/2005 | Mann |
| 2005/0227775 A1 | 10/2005 | Cassady et al. |
| 2005/0261073 A1 | 11/2005 | Farrington et al. |
| 2006/0025229 A1* | 2/2006 | Mahajan ............ A63B 24/0003 473/131 |
| 2006/0052173 A1 | 3/2006 | Telford |
| 2006/0166737 A1 | 7/2006 | Bentley |
| 2006/0166738 A1 | 7/2006 | Eyestone et al. |
| 2006/0184336 A1 | 8/2006 | Kolen |
| 2006/0277466 A1 | 12/2006 | Anderson |
| 2007/0015611 A1 | 1/2007 | Noble et al. |
| 2007/0026975 A1 | 2/2007 | Marty et al. |
| 2007/0105664 A1 | 5/2007 | Scheinert et al. |
| 2007/0111811 A1 | 5/2007 | Grober |
| 2007/0135225 A1 | 6/2007 | Nieminen et al. |
| 2007/0207873 A1 | 9/2007 | Rose |
| 2007/0265105 A1 | 11/2007 | Barton et al. |
| 2008/0085778 A1 | 4/2008 | Dugan |
| 2008/0200287 A1 | 8/2008 | Marty et al. |
| 2008/0312010 A1 | 12/2008 | Marty et al. |
| 2009/0143926 A1 | 6/2009 | Almalki et al. |
| 2009/0209358 A1 | 8/2009 | Niegowski |
| 2009/0210078 A1 | 8/2009 | Crowley |
| 2010/0093463 A1 | 4/2010 | Davenport et al. |
| 2010/0121228 A1 | 5/2010 | Stirling et al. |
| 2010/0144414 A1 | 6/2010 | Edis et al. |
| 2010/0173276 A1 | 7/2010 | Vasin |
| 2010/0184564 A1 | 7/2010 | Molyneux et al. |
| 2010/0323794 A1 | 12/2010 | Su |
| 2011/0021280 A1 | 1/2011 | Boroda et al. |
| 2011/0054290 A1 | 3/2011 | Derchak |
| 2011/0143319 A1 | 6/2011 | Bennett et al. |
| 2011/0183787 A1 | 7/2011 | Schwenger et al. |
| 2011/0184225 A1 | 7/2011 | Whitall et al. |
| 2011/0202152 A1 | 8/2011 | Barton et al. |
| 2011/0230265 A1 | 9/2011 | Amit |
| 2011/0230274 A1 | 9/2011 | Lafortune et al. |
| 2012/0029666 A1 | 2/2012 | Crowley et al. |
| 2012/0046119 A1 | 2/2012 | Davenport |
| 2012/0050529 A1 | 3/2012 | Bentley |
| 2012/0052973 A1 | 3/2012 | Bentley |
| 2012/0136464 A1 | 5/2012 | Saito et al. |
| 2012/0157241 A1 | 6/2012 | Nomura et al. |
| 2012/0189996 A1 | 7/2012 | Hager et al. |
| 2012/0236030 A1 | 9/2012 | Border et al. |
| 2013/0018493 A1 | 1/2013 | Amini |
| 2013/0018494 A1 | 1/2013 | Amini |
| 2013/0053190 A1* | 2/2013 | Mettler ............... A63B 24/0062 473/463 |
| 2013/0095939 A1 | 4/2013 | Meadows et al. |
| 2013/0095962 A1 | 4/2013 | Yamamoto et al. |
| 2013/0128022 A1 | 5/2013 | Bose et al. |
| 2013/0266918 A1 | 10/2013 | Tinjust |
| 2013/0267339 A1 | 10/2013 | Boyd et al. |
| 2013/0302768 A1 | 11/2013 | Webb |
| 2014/0031703 A1 | 1/2014 | Rayner et al. |
| 2014/0047457 A1 | 2/2014 | Nojima |
| 2014/0278219 A1 | 9/2014 | Canavan et al. |
| 2015/0019135 A1 | 1/2015 | Kacyvenski et al. |
| 2015/0057111 A1 | 2/2015 | Tremblay-munger et al. |
| 2015/0104768 A1 | 4/2015 | Clark |
| 2015/0112464 A1 | 4/2015 | Crowley et al. |
| 2015/0120021 A1 | 4/2015 | Kerhuel et al. |
| 2015/0141178 A1 | 5/2015 | Mettler |
| 2015/0196803 A1 | 7/2015 | Shavit et al. |
| 2015/0317910 A1 | 11/2015 | Daniels |
| 2016/0027325 A1 | 1/2016 | Malhotra |
| 2016/0086500 A1 | 3/2016 | Kaleal |
| 2016/0303426 A1 | 10/2016 | Martikka et al. |
| 2016/0361593 A1 | 12/2016 | Elliott |
| 2017/0004358 A1 | 1/2017 | Bose et al. |
| 2017/0011527 A1 | 1/2017 | Matsunaga et al. |
| 2017/0021259 A1 | 1/2017 | Dismuke |
| 2017/0061817 A1 | 3/2017 | Mettler May |
| 2017/0225033 A1 | 8/2017 | Czaja |
| 2017/0232324 A1 | 8/2017 | Mettler May |
| 2018/0001173 A1 | 1/2018 | Cupa |
| 2018/0229078 A1 | 8/2018 | Mettler |
| 2019/0009133 A1 | 1/2019 | Mettler May |
| 2019/0111327 A1 | 4/2019 | Mochizuki |
| 2019/0126126 A1 | 5/2019 | Knab |

(56) References Cited

U.S. PATENT DOCUMENTS

| | | | |
|---|---|---|---|
| 2020/0289907 A1 | 9/2020 | Mettler May | |
| 2021/0110734 A1 | 4/2021 | Mettler May | |

FOREIGN PATENT DOCUMENTS

| | | | |
|---|---|---|---|
| EP | 2752224 A1 | 7/2014 | |
| FR | 2829700 A1 | 3/2003 | |
| RU | 2364436 C2 | 8/2009 | |
| WO | 2006004908 A2 | 1/2006 | |
| WO | 2009043558 A1 | 4/2009 | |
| WO | 2011036567 A2 | 3/2011 | |
| WO | 2015123474 A1 | 8/2015 | |
| WO | 2016025460 A1 | 2/2016 | |
| WO | 20170420242 A1 | 3/2017 | |

OTHER PUBLICATIONS

Dec. 7, 2020 summons to attend oral proceedings for European patent application No. 15831843.6, 7 pages.
Office Action dated Dec. 7, 2020 in connection with Chinese Patent Application No. 2016800641099, 5 pages including English translation.
Extended European Search Report dated Feb. 10, 2021 in connection with European patent application No. 18829049.8, 7 pages.
Extended European Search Report dated Jun. 21, 2018 in connection with European Patent Application No. 18173631.5, 4 pages.
Office Action dated Jul. 25, 2019 in connection with Chinese Patent Application No. 2016800641099, 17 pages including English translation.
Decision Denying Institution of Inter Partes Review; IPR2016-00675, U.S. Pat. No. 8,941,723. 16 pages, Aug. 14, 2017.
Final Written Decision of Inter Partes Review; IPR2016-00676, U.S. Pat. No. 8,905,855. 38 pages, Aug. 14, 2017.
Final Written Decision of Inter Partes Review; IPR2016-00677, U.S. Pat. No. 8,944,928. 30 pages, Aug. 14, 2017.
Decision Denying Institution of Inter Partes Review; IPR2016-00672, U.S. Pat. No. 8,903,521. 20 pages, Aug. 29, 2016.
Decision Denying Institution of Inter Partes Review; IPR2016-00674, U.S. Pat. No. 9,039,527. 11 pages, Aug. 29, 2016.
Otto, et al. "System Architecture of a Wireless Body Area Sensor Network for Ubiquitous Health Monitoring," Journal of Mobile Multimedia, vol. 1, No. 4, 2006, pp. 307-326.
Decision Denying Request for Rehearing; IPR20198-00537, U.S. Pat. No. 8,831,905. 8 pages, Oct. 7, 2019.
Decision Denying Petitioner's Request for Rehearing of Decision Denying Institution of Inter Partes Review; IPR2019-00538, U.S. Pat. No. 8,589,114. 12 pages, Oct. 10, 2019.
Decision Denying Petitioner's Request for Rehearing of Decision Denying Institution of Inter Partes Review; IPR2019-00536, U.S. Pat. No. 9,656,122. 14 pages, Oct. 24, 2019.
Second Office Action dated May 19, 2020 in connection with Chinese Patent Application No. 2016800641099, 23 pages including English translation.
Communication Pursuant to Article 94(3) EPC dated Feb. 1, 2016 in connection with European Patent Application No. 12827395.0.
Examination Report dated May 22, 2019 in connection with European Patent Application 15831843.6, 6 pages.
Extended European Search Report dated Apr. 21, 2015 in connection with European Patent Application No. 12827395.0, 6 pages.
Extended European Search Report dated Apr. 8, 2019 in connection with European Patent Application No. 16842664.1, 13 pages.
Extended European Search Report dated Nov. 29, 2017 in connection with European Patent Application No. 15831843.6, 10 pages.
International Search Report and Written Opinion dated Nov. 11, 2015 in connection with International Patent Application No. PCT/US2015/044620, 12 pages.
International Search and Written Opinion dated Nov. 20, 2018 in connection with International Patent Application No. PCT/US2018/041118, 12 pages.
International Search Report and Written Opinion dated Mar. 9, 2017 in connection with International Patent Application No. PCT/US2016/048871, 16 pages.
Abernathy, et al., "Expertise and the perception of kinematic and situational probability information", Abstract, Perception, 2001; 30(2): 233-252.
Bernardi, et al., "Mental practice promotes motor anticipation: evidence for skilled music performance", Abstract, Frontiers in Human Neuroscience, 2013; 7:451.
Bernstein, "The Co-ordination and Regulation of Movements", Science, Jan. 26, 1968: vol. 159, Issue 3813, p. 415.
Gibson, "The Ecological Approach Io Visual Perception: Classic Edition", Introduction, Psychology Press, 1986.
Kugler, et al., "Information, natural law, and the self-assembly of Yhythmic movement", Abstract, Hillsdale, N.J., NJ Erlbaum Associates, (1987).
Landlinger, et al., "Key factors and timing patterns in the tennis forehand of different skill levels", J. Sports Sc. & Med., 9(4): 643 (2010).
Lee, et al., "Sensory and intrinsic coordination of movement", Royal Soc. of London, pp. 2029-2035 (1999).
Posner, et al., "Orienting of Attention", The Quarterly Journal of Experimental Psychology, 1980, 32:3-35.
Warren, "The Dynamics of Perception and Action", Psychological Review, (2006), vol. 113, No. 2, pp. 358-389.
Williams, et al., "Anticipation skill in a real-world task: Measurement, raining, and transfer in tennis", Abstract, Journal of Experimental Psychology: Applied, vol. 8(4), Dec. 2002, pp. 259-270.
Office Action dated Dec. 7, 2021 in connection with European patent application No. 16842664.1, 11 pages.
Second Office Action dated Jan. 6, 2022 in connection with Chinese patent application No. 2018800486618, 9 pages including English translation.
Official Action dated Mar. 1, 2022 in connection with European patent application No. 18829049.8, 13 pages.
Decision of Rejection dated Jun. 1, 2022 in connection with Chinese patent application No. 2018800486618, 12 pages including English translation., Jun. 1, 2022.

* cited by examiner

CODIFICATION AND CUEING SYSTEM FOR SPORT AND VOCATIONAL ACTIVITIES

CROSS REFERENCE TO RELATED APPLICATIONS

This application is a continuation of U.S. patent application Ser. No. 15/502,612, filed Feb. 8, 2017, "Codification and Cueing System for Sport and Vocational Activities," issued Jun. 2, 2020 as U.S. Pat. No. 10,668,353 B2, which claims priority to international Patent Application PCT/US2015/044620, filed Aug. 11, 2015, "Codification and Cueing System for Human Interactions in Tennis and other Sport and Vocational Activities," and U.S. Provisional Application No. 62/035,569, filed Aug. 11, 2014, "Codification System for Tennis Timing and Technique to Provide Interactive Temporal Player Cuing," each of which is incorporated herein by reference herein.

BACKGROUND

Timing of actions represents a fundamental factor for many aspects of human behavior. Lee, "Sensory and intrinsic coordination of movement," Royal Soc. of London, 2029-2035 (1999). In tennis, as well as in other sports or vocational activities involving coordination of complex movements or actions, timing is essential to the smooth flow of performance during a game or activity. The timing encompasses broad aspects of the activity. For example in tennis, timing is involved in game elements ranging from court motion, posture and stance, and attention allocation, to stroke preparation and execution (see Landlinger, "Key factors and timing patterns in the tennis forehand of different skill levels," J. Sports Sci. & Med. 9(4): 643 (2010), which provides an investigation of key kinematic features and their timing in forehand strokes).

Execution of properly timed actions relies heavily on perceptual processes that provide the cues necessary for planning and timing of these actions. This action-perception cycle is a dynamic system (see Kugler, Information, natural law, and the self-assembly of rhythmic movement, Erlbaum Associates, Hillsdale, N.J. (1987), and Warren, "The dynamics of perception an action," Psychological review 113.2 358 (2006)).

Moreover, this system forms an interactive process that can encompass the behavior of multiple actors and their interaction with their environment and task elements. In tennis for example, timing of actions, and plans of future actions are adapted continuously based on the outcome of those actions in the task or activity environment, and the adversary's reaction to one's own actions. Similar challenges are also present in cooperative situations such as the behavior of another team member in an operating room, where safe and efficient workflow requires the surgical team members to be able to correctly anticipate the timing and type of future actions.

Timing is a dynamic dimension that should be adapted to the continuous changes in an activity to achieve effective sequences of coordinated actions (e.g., court and stroke motions in tennis). Acquiring the skills to properly coordinate these processes is one of the most fundamental challenges for learning and performing in interactive multi-actor sports or similar activities.

Complex human movements involve the coordination of many degrees of freedom (muscles and joints) and often unfold too fast to be amenable to continuous feedback. Many activities involve action selection and implementation within fraction of a second, and proper execution requires synchronization down to milliseconds in some activities (Bernardi et al., "Mental practice promotes motor anticipation: evidence from skilled music performance," Frontiers in Human Neuroscience 7 (2013)). For example, a high-performance tennis stroke requires efficient transfer of momentum to the ball via the kinematic chain going from the legs, hip, core, to upper body and arms, and finally, the racket (racquet). This entire chain of movements is implemented as a pattern and unit of movement for that particular stroke.

Therefore, these complex human movements cannot be produced instantaneously but rather rely on learned motion patterns. Once learned, these patterns are stored in procedural memory and act as units of organization for larger motion behaviors and interactions with the environment or other subjects or actors (see Bernstein, The co-ordination and regulation of movement, Pergamon, N.Y. (1967)).

Timing of these patterns plays a critical role in performance. Since the movement patterns are not instantaneous but of finite durations, their successful execution requires anticipation of the future actors' behavior and interactions in a particular activity. Therefore, their execution relies on the identification of cues that support the selection of the appropriate behavior pattern and the timing necessary for proper execution. In other words, effective performance in activities involving complex interactions with environments and other actors relies on a spatio-temporal structure that supports the coordination of events and facilitates advanced planning and organization.

For example, in tennis the players rely on characteristic patterns of play to extract anticipatory cues that help predict the future ball trajectory and player behavior. This information is then used to select and start the execution of the appropriate court and stroke movements. With adequate court positioning, posture, and stroke, the player can then optimally execute the associated units of movements.

Timing, preparation, and initiation of the tennis stroke and supporting units of movement, such as court positioning, are based on cues extracted from the environment which encompasses court and game events, such as the impact of the ball on the ground, as well as cues extracted from the adversary's behavior such as the adversary's stroke and racket-ball contact. These cues make it possible to predict the future ball trajectory and pattern of play in the adversary's game plan.

For tennis, the timing information about an adversary's return is one of the most basic cue, since up to the instant of impact it is difficult to predict the adversary's intended stroke placement on the court and the ball's pace and effect (i.e. spin). The impact therefore represents a primary focus of attention. The impact's strength and direction provides information useful for the prediction of the ball's trajectory which in turn is used to plan and initiate the sequence of stroke selection, preparations, and necessary body posture and court positioning.

Studies investigating tennis player's visual attention, however, have shown that advanced players are able to utilize early cues including the opponent's body stance, stroke preparation and initiation, while beginners tend to use later cues such as the oncoming ball's trajectory. Abernathy, "Expertise and the perception of kinematic and situational probability information," Perception (London), 30(2): 233-252 (2001); Williams, "Anticipation skill in a real-world task: measurement, training, and transfer in tennis," J. of Exp. Psych: Appl. 8(4): 259 (2002).

Beginners therefore are mostly challenged by the large amount of information available in a task environment. Advanced actors are able to filter through this information on the most relevant cues, but still can be prone to stress, distraction and effects of fatigue.

Humans and other animals can use a broad range of sensing and perception abilities, including the auditory and visual systems, to extract cues necessary to achieve effective planning and timing of actions. From the standpoint of ecological psychology some of these cues are readily available from the subject's direct perceptual experience of the environment interaction (Gibson, The Ecological Approach to Visual Perception: Classic Edition, Psychology Press (2014)).

Perceptual mechanisms in complex tasks depend on various cognitive mechanisms in particular attention (Posner, "Orienting of attention," Quarterly Journal of Experimental Psychology 32, no. 1: 3-25 (1980)). Cueing therefore can help by focusing attention on relevant events in a task environment. In tennis, for example, a cueing (cuing) system can be used to enhance attention to the major court events and relevant aspect of an adversary's behavior. A rudimentary behavioral aid used by some players is counting from 1 to 3. A player would count "1" at the adversary's ball contact, "2" at the bounce of the ball in the court, and "3" when striking the ball. This technique ostensibly supports the organization and coordination of the player's perceptual and motor processes.

What is needed are tools that help actors or players maintain timing and/or focus attention in interactive vocational performance and sports.

SUMMARY

Disclosed are codification systems and methods to provide cues in real-time to actors, users, players or participants in an interactive sport or vocational activity using information extracted from measurements of a relevant participant's behavior and environmental interactions. The extracted information is used to predict relevant outcomes of the activity and transform these into cues that can be communicated to the participant via auditory, haptic, and/or visual stimuli. The codification system describes the spatial and temporal characteristics of key events and provides the basis for game and user performance analysis as well as the determination of interaction models and cueing laws. The cueing technology augments the actors' interaction by providing timing cues that help direct attention to the relevant environment cues. At the same time, it can encode additional information to help users select, plan and execute their actions. It can be used both for training as well as a performance augmentation. The systems are illustrated in a tennis application. In this example, the codification system, for example, describes the ball trajectory, court events, player behavior and racket motion. In this example, cueing signals are designed to help the participant prepare their stroke, direct their attention to the relevant cues, as well as, embed additional information that help anticipate the adversary's shot types.

Moreover, this system forms an interactive process that can encompass the behavior of multiple agents and their interaction with their environment and task elements. For example in tennis, the timing of actions and decisions are adapted based on the adversary's reaction to one's own actions and the adversary's game and tactics. Similar challenges are also present in cooperative situations such as the behavior of other team members in a surgical theater.

An aspect of the disclosure is directed to a cueing device. Cueing devices comprise: two or more sensors wherein the two or more sensors are selected from the group comprising an inertial sensor, a magnetometer, an acoustic sensor, a string bed deformation sensor, a strain gauge sensor, an optical sensor, and a light sensor; a processor in communication with the two or more sensors, wherein the processor is configured to analyze data from the two or more sensor and generate one or more instructions; and a cue administrator configurable to generate one or more cues based on the one or more instruction from the processor. In some configurations, a securement device is provided for securing the cueing device to another object, such as a racket. The cue administrator can be one or more of a speaker, a light emitter, and a vibration generator. The cue administrator can be incorporated into the cueing device or be in communication with the cueing device. Additionally, a wireless transmitter can be provided. A wireless transmitter can be configurable to communicate with at least one secondary device which is remote from the cueing device. Suitable secondary devices include one or more of a second cueing device, a smart phone, and a tablet. The secondary devices can, among other functional features, measure environmental information. Additionally, the cue administrator generates the cue based on two or more of detection of a movement, extraction of a movement data, prediction of a movement outcome, processing of movement information.

Still another aspect of the disclosure is directed to a means for cueing. Suitable means for cueing comprise: a housing; two or more sensing means wherein the two or more sensing means are selected from the group comprising an inertial sensor, a magnetometer, an acoustic sensor, a string bed deformation sensor, a strain gauge sensor, an optical sensor, and a light sensor; a processing means in communication with the two or more sensing means, wherein the processing means is configured to analyze data from the two or more sensing means and generate one or more instructions; a cue administrator configurable to generate one or more cues based on the one or more instruction from the processing means; and a means for providing power. Additionally, a securement device for securing the means for cueing to another piece of equipment such as a racket can be provided. The cue administrator can be one or more of a speaker, a light emitter, and a vibration generator. Additionally, a wireless transmitter can be provided. Configurations with a wireless transmitter are configurable so that the wireless transmitter communicates with at least one secondary device. Secondary devices can be one or more of a second cueing device, a smart phone, and a tablet. The secondary devices can, among other functional features, measure environmental information. Additionally, the cue administrator is configurable to generate the cue based on two or more of detection of a movement, extraction of a movement data, prediction of a movement outcome, processing of movement information.

Yet another aspect of the disclosure is directed to a cueing system. Cueing systems comprise: a first cueing device having two or more first cueing device sensors wherein the first cueing device two or more sensors are selected from the group comprising an inertial sensor, a magnetometer, an acoustic sensor, a string bed deformation sensor, a strain gauge sensor, an optical sensor, and a light sensor, a first cueing device processor in communication with the two or more sensors, wherein the first cueing device processor is configured to analyze data from the first cueing device two or more sensor and generate one or more instructions, and a first cueing device cue administrator configurable to generate one or more cues based on the one or more instruction from the processor; and a second cueing device having two or more second cueing device sensors wherein the second cueing device two or more sensors are selected from the group comprising an inertial sensor, a magnetometer, an acoustic sensor, a string bed deformation sensor, a strain gauge sensor, an optical sensor, and a light sensor, a second cueing device processor in communication with the two or more sensors, wherein the second cueing device processor is configured to analyze data from the second cueing device two or more sensor and generate one or more instructions, and a second cueing device cue administrator configurable to generate one or more cues based on the one or more instruction from the processor.

In some configurations of the system, at least one of a first cueing device securement device for securing the first cueing device to another device such as a first racket, and a second cueing device securement device for securing the second cueing device to another piece of equipment, different than the first device, such as a second racket. Additionally, the first cue administrator or second cue administrator can be one or more of a speaker, a light emitter, and a vibration generator. In at least some configurations of the system, a wireless transmitter is provided. The wireless transmitter is further configurable to communicate with at least one secondary device, wherein the secondary device is remote from the first cueing device and the second cueing device. The at least one secondary device can be, for example, a smart phone, and a tablet. Moreover, the cue administrator can be configurable to generate the cue based on two or more of detection of a movement, extraction of a movement data, prediction of a movement outcome, processing of movement information.

Another aspect of the disclosure is directed to a method for cueing a participant in an environment. The method of cueing comprises: obtaining from a first cueing device having two or more sensors wherein the two or more sensors are selected from the group comprising an inertial sensor, a magnetometer, an acoustic sensor, a string bed deformation sensor, a strain gauge sensor, an optical sensor, and a light sensor at least two sensed data; analyzing the obtained data; predicting a movement outcome from the analyzed data; and generating an instruction to issue a cue. Additionally, the method can include securing the first cueing device to a racket. In some configurations of the method, the cueing device can communicate with at least one secondary device. Suitable secondary devices include one or more of a second cueing device, a smart phone, and a tablet. The cue administrator can be configured to generate the cue based on two or more of detection of a movement, extraction of a movement data, prediction of a movement outcome, processing of movement information.

INCORPORATION BY REFERENCE

All publications, patents, and patent applications mentioned in this specification are herein incorporated by reference to the same extent as if each individual publication, patent, or patent application was specifically and individually indicated to be incorporated by reference. Prior references include, for example, US 2013/0053190 A1 published Feb. 28, 2013, for Racket Sport Inertial Sensor Motion Tracking and Analysis, now U.S. Pat. No. 8,944,940 B2 issued Feb. 3, 2015; U.S. Pat. No. 8,602,922 B2 issued Dec. 10, 2013, for Method and Apparatuses for Enhancing Performance in Racket Sports, US 2005/0017454 A1 published Jan. 27, 2005, for Interactive Gaming Systems with Haptic Feedback; US 2007/0105664 A1 published May 10, 2007, for Racquet with Entertainment and Performance Feedback; U.S. Pat. No. 4,257,594 A issued Mar. 24, 1981, for Electronic Athletic Equipment; U.S. Pat. No. 8,337,335 B2 issued Dec. 25, 2012, for Systems and Methods for Measuring and/or Analyzing Swing Information; U.S. Pat. No. 5,646,911 A issued Jul. 8, 1997, for Tennis Pacer; U.S. Pat. No. 5,226,650 A issued Jul. 13, 1993, for Tennis Racket; US 2002/0077189 A1 published Jun. 20, 2002, for Proprioceptive Golf Club with Analysis, Correction and Control Capabilities; U.S. Pat. No. 5,031,909 A issued Jul. 16, 1991, for Electronic Athletic Equipment; US 2006/0025229 A1 published Feb. 2, 2006, for Motion Tracking and Analysis Apparatus and Method and System Implementations Thereof; U.S. Pat. No. 4,303,241 A issued Dec. 1, 1981, for Sports Vision Training Device; U.S. Pat. No. 7,891,666 B2 issued Feb. 22, 2011, for Device and Method for Measuring Shot Force Exerted on a Moveable Game Device; and WO 2009/043558 A1 published Apr. 9, 2009, for Force Sensor for Racquet Handle.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Disclosed are devices, systems and methods to provide objective and easily recognizable cues in real-time to one or more actors engaged in an activity using information extracted from measurements of their behavior and the task environment.

Figure 10:
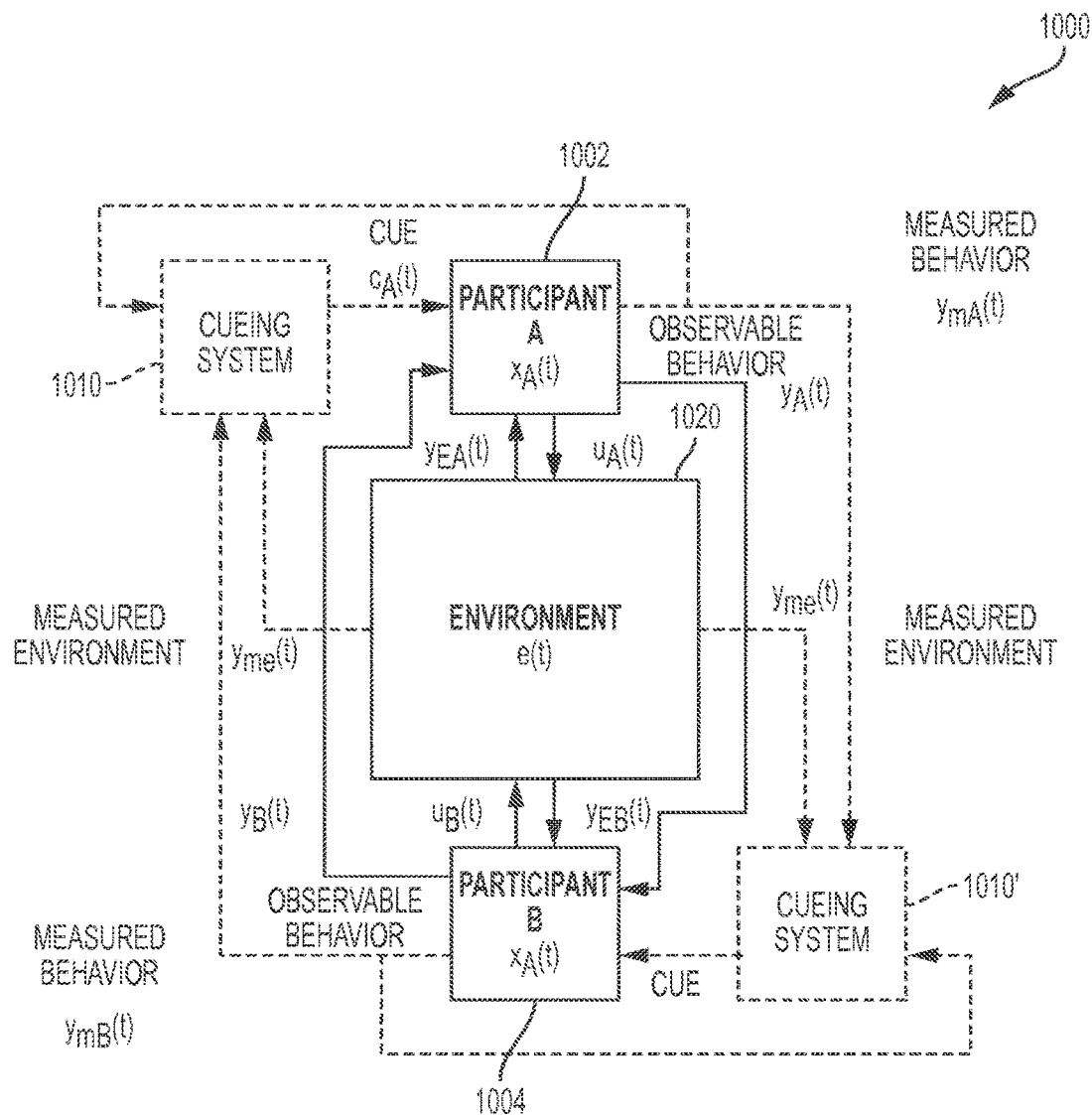
FIG. 10 illustrates a closed-loop interaction between two users and a task environment augmented by a cueing systems.

FIG. 10 illustrates an interaction between participants within a task environment 1000 and the cueing system (in dashed) 1010, 1010'. The environment 1020, described by a state variable e(t), represents the system that mediates the behavior. For example, the environment could be a tennis court or a surgical theater. The actions or behavior of two participants, player A (1002) and player B (1004), are denoted by uA(t) and uB(t) which affects environment state e(t) and the evolving state, in turn, influences the each participants' behavior. The participants determine their behavior both from observations of the other participant(s), yA(t) or yB(t) respectively, and observations of the environment, yEA(t) and yEB(t) respectively. Every participant has their own observation of the environment. Each participant's decision and behavior is generally also influenced by their own state $x_A(t)$ or $x_B(t)$. The dynamics of an activity are described by an interaction model that describes how the participant's behavior and actions affect the environment. Such models are typically based on statistical methods such as hidden Markov models or Bayesian networks.

As will be appreciated by those skilled in the art, this model could be extended to arbitrary number of participants. With more than two participants, the topology of the interactions, i.e. how participant's actions affect other participants and the environment and which participants are observable, etc., may need to be specified.

The cueing systems 1010, 1010' in FIG. 10 take measurements from the environment $y_{me}(t)$ and the participants 1002, 1004, $y_{mA}(t)$ $y_{mB}(t)$, and use the activity's interaction model to determine the cues that will help the participants 1002, 1004 individual performance as well as the overall performance in activity which they are engaged.

Figure 9:
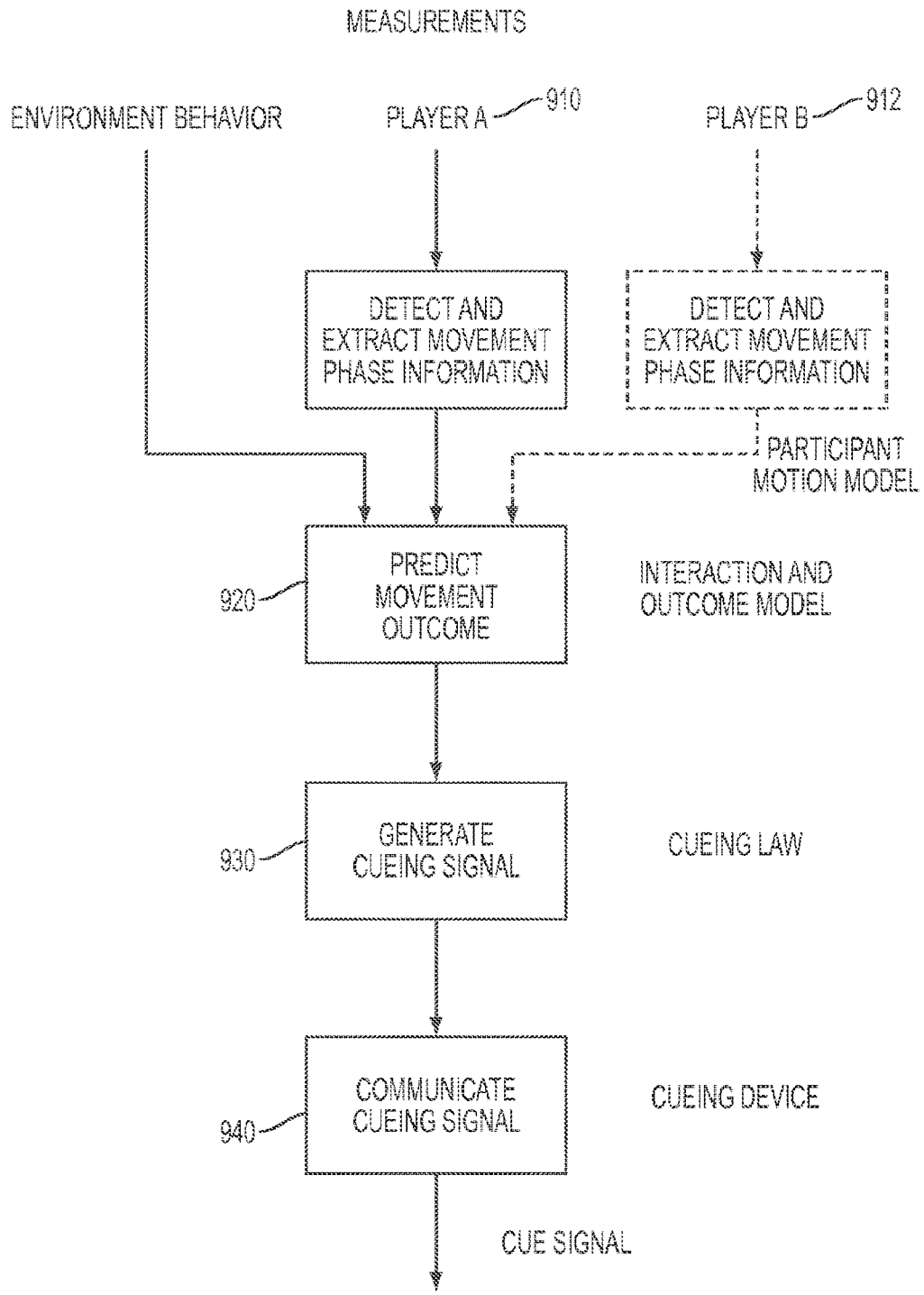
FIG. 9 illustrates the general processes and data flow associated with the cueing system, starting with the measurement data and proceeding through the detection of the relevant user behavior (e.g., movement phases), extraction of their attributes of the user's behavior, the prediction of the outcome of the user's behavior in the environment, generation and communication of the cueing signal.

FIG. 9 illustrates general processes and data flow associated with the cueing system, starting with the measurement data and proceeding through the detection of the relevant movement phases, extraction of attributes, the prediction of the movement outcome, generation and communication of cueing signals. The cueing system is exemplified for racket sport players. The information extracted from the environment include court events such as the ball trajectory relative to the court. Information extracted from the other player behavior, include body and racket motion. This information is used by the players to determine their behavior. A cueing system uses measurement of these quantities to generate cue signals for the players $c_A(t)$ and $c_B(t)$.

The cueing system combines several steps. During a first step, detection of environment and behavioral events based on characteristic features available in measurements is determined. The features typically correspond to a manifestation of a particular action in the kinematics or dynamics of the behavior. For example, consider the acceleration of a racket head during a backswing or forward swing initiation, or the impulsive acceleration resulting from the racket-ball strike. During a second step, extraction and estimation of attributes associated with the event including temporal and state information, e.g., the time of racket-ball impact or the maximum racket acceleration. During a third step, prediction of the outcome associated with the event in the environment, e.g., prediction of the speed or trajectory of the ball relative to the court and determination of the impact location. During a fourth step, a cue signal is generated from the predicted motion or action outcome and the state of the participants. Finally, the cue stimulus is communicated to the participants.

The system is configurable to detect and extract movement phase information for participants A (910). Additionally, the system is configurable to detect and extract movement phase information for Player B (912). The detected and extracted movement information is analyzed to predict movement outcome 920. Additionally, the movement outcome prediction can incorporate environment and behavior information 914. Once the movement outcome is predicted, a cueing signal is generated 930. Thereafter the cueing signal is communicated 940.

Steps 1 and 2 are typically described by the motion (behavior) models. Note that the two steps can often be combined as a single step without departing from the scope of the disclosure. Step 3 is described by an outcome and interaction model. In general, the outcome of an action by one actor also depends on the state of the one or more other users (shown in dashed in FIG. 9). Therefore, the outcome model and interaction model should account for these effects when the effects of the outcome associated with an event is significant. Step 4 corresponds to the cueing or feedback law. Step 4 is implementable by a cueing device. Note that the measurement of the behavior is not illustrated in FIG. 9. The measurement of behavior can be obtained from different systems (worn by the individual subjects, or available on the sports field or operating theater, etc.). Most sports or vocational activities involve patterns of interactions. In some cases, these interactions involve periodic patterns that have distinct timing events that are critical to the smooth performance of the activity.

For example, in racket sports, distinct timing events in the players' interactions can be identified. The most recognizable events are: the instant of a ball's impact on the player's racket, the ball's net crossing, and the bouncing of the ball on the ground. Humans combine these events in ways that form units of behavior.

Figure 15:
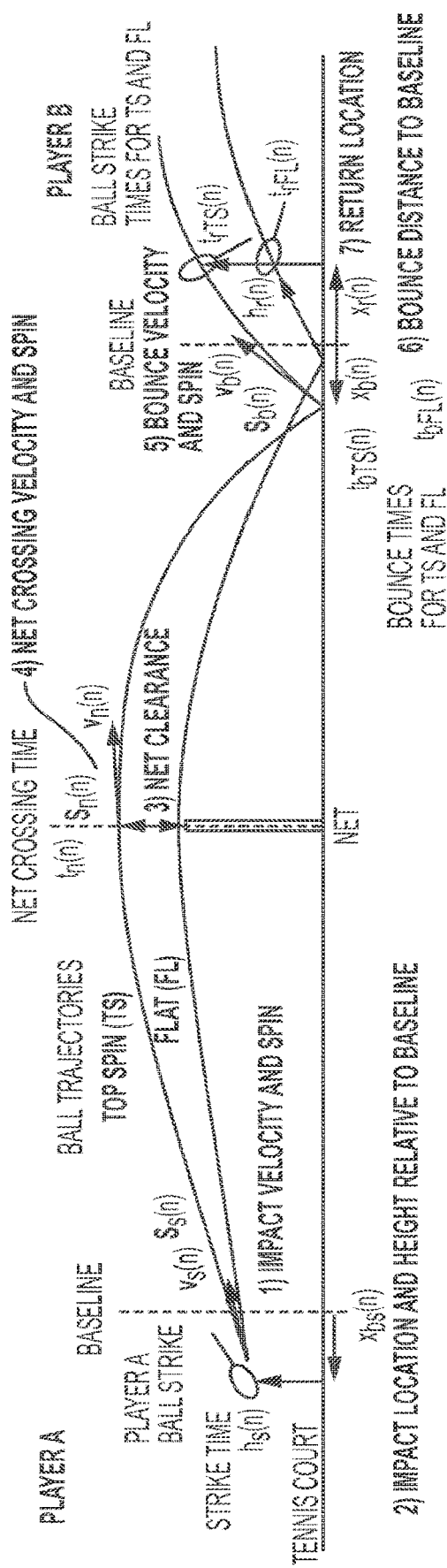
FIG. 15 shows the ball trajectory for a topspin (TS) and flat (FL) stroke by player A and highlights the primary impact and outcome variables including: impact velocity and spin (e.g. TS), impact location, net clearance, net crossing velocity and spin, bounce velocity and spin and the distance to baseline. The figure also illustrates how two different strokes result in different impact conditions for the receiving player B.

FIG. 15 shows the longitudinal-vertical view of an exemplar ball trajectory for a topspin (TS) and flat (FL) stroke by player A and highlights the primary impact and outcome variables for the TS trajectory including: impact velocity $v_s(n)$, spin $S_n(n)$ and height $h_s(n)$ and distance from baseline $x_s(n)$; net clearance $h_n(n)$, crossing velocity $v_n(n)$ and spin $S_n(n)$; bounce $v_b(n)$, spin $S_b(n)$ and height $h_b(n)$, and distance from baseline $x_b(n)$. The figure also indicates the stroke time $t_s(n)$, net clearance time $t_n(n)$, bounce time $t_b(n)$ and return time $t_r(n)$.

FIG. 15 shows how the TS and SL trajectories result in different impact conditions for the receiving player B. Since players rely in part on ecological perceptual mechanisms to interact with their environment, as well as higher-level perceptual mechanisms that rely on attention processes. They may use a wide range of visual phenomena (possibly also auditory) to extract cues that will help identify the stroke type and anticipate the ball trajectory. Ecological cues may be the patterns contained in the combination of visual flow and sound resulting from the oncoming ball bouncing on the ground. This information is used for the stroke timing and execution shortly before impact. Higher-level cues may be the adversary's pattern in stroke movement. This latter information, is processed and used to coordinate court movement and positioning, prepare the return stroke, and make the adjustments necessary to achieve the desired trajectory outcomes in relationship to their respective game plans. The exact combination of processes depends on the skill level and other individual factors.

Figure 1:
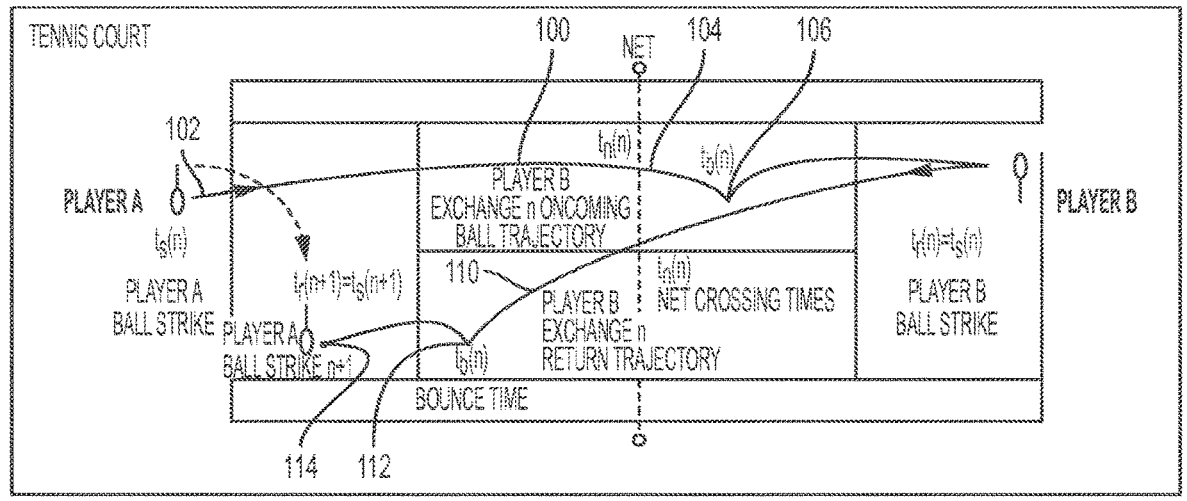
FIG. 1 is a depiction of an example of a task or activity environment for tennis. The figure illustrates exemplar events which are determined by the ball's trajectory off the ball relative to the tennis court for an exchange T(n) between player A and player B.

FIG. 1 depicts the top-down view of an exemplar exchange showing an initial trajectory 100 of the ball 102 during play and key game events. Player A strikes a ball 102 which crosses the net 104. The ball may have an initial bounce 106 before being hit by Player B. Player B strikes the ball, which then crosses the net following a second trajectory 110. The ball can then hit the ground 112 before being hit again 114 by Player A.

Figure 2:
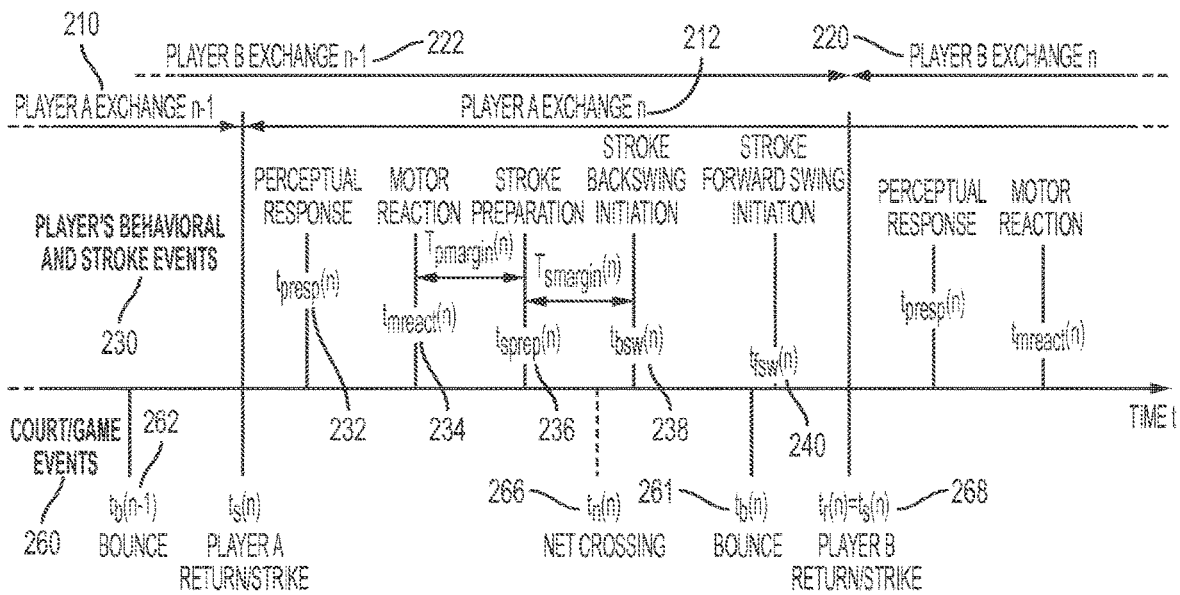
FIG. 2 illustrates an events history for tennis exchanges divided into environment events, e.g. court/game events, and player's behavioral events.

FIG. 2 depicts the sequence of events as a time history. The sequence is arranged on an x-axis as player A exchange n−1 (210), player A exchange n (212), player B exchange b (220), and player B exchange n−1 (222). On the y-axis, events are divided between player's behavioral and stroke events 230, and court/game events 260. The player's behavioral and stroke events 230 for player A exchange n (212), which includes the perceptual response 232 ($t_{presp}(n)$), the motor reaction 234 ($t_{mreact}(n)$), the stroke preparation 236 ($t_{sprep}(n)$), the stroke backswing initiation 238 ($t_{bsw}(n)$), and the stroke forward swing initiation 240 ($t_{fsw}(n)$). The distance between the motor reaction 234 ($t_{mreact}(n)$) and the stroke preparation 236 ($t_{sprep}(n)$) is $T_{pmarg}(n)$, and the distance between the stroke preparation 236 ($t_{sprep}(n)$) and the stroke backswing initiation 238 ($t_{bsw}(n)$) is $T_{smarg}(n)$.

Court game events 260 include the bounce 262 ($t_b(n-1)$), the player A return/strike 264 ($t_s(n)$), the net crossing 266 ($t_n(n)$) which occurs at a time between the stroke preparation 236 ($t_{sprep}(n)$) and the stroke backswing initiation 238 ($t_{bsw}(n)$). The bounce 261 ($t_b(n)$) which occurs before the stroke forward swing initiation 240, and the player B return strike 268 ($t_r(n)=t_s(n)$).

The spatial and temporal patterns associated with the events provide a structure, i.e., a form of "scaffold," for the organization of the performance. These cues provide synchronization and rhythm that are helpful for the organization of the different aspects of performance including sensory, perceptual and movement. Accurate perception of the more basic events provides directions for the attention and therefore is essential for the acquisition of more detailed cues that provide additional information such as needed for predicting outcomes of events. The design of cueing system should account for the basic principles of human information processing.

Figure 13:
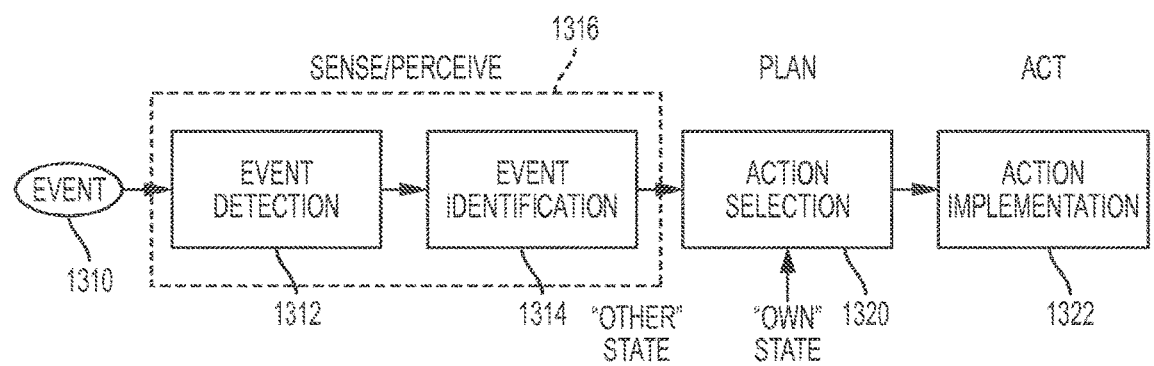
FIG. 13 illustrates a model human "sense-plan-act" process. It describes the onset of an event, the detection of the event, identification and selection of an action, and implementation of the action.

For example, FIG. 13 describes the steps from the event occurrence 1310, its detection 1312, identification, 1314 (part of sensing/perceiving 1316), culminating with the action selection 1320 and execution of an action 1322. This simple serial model is common in cognitive sciences and is also related on the Sense Plan Act model in robotics. More recent evidence points to parallel brain processing. The serial model provides a practical and often still valid framework.

Possibly one of the most important parameters in human behavior is reaction or response time. Kosinski, A literature review on reaction time, Clemson University, 10 (2008). Response time represents the time duration between a stimulus and the subject's response to that stimulus. The reaction time varies based on the sensory modality (typically visual, auditory and haptic) and type of stimulus and response. The stimuli are typically classified as simple, choice and recognition stimuli. Auditory stimuli elicit faster responses than visual (mean auditory reaction times of 0.14-0.16 seconds vs. mean visual reactions times of 0.18-0.2 seconds). For recognition and choice experiments, an important factor is the number of possible stimuli (e.g. letter in a symbol recognition). For a number of possible stimuli N the reaction time is proportional to log N or N depending on the studies.

Given the basic knowledge of human information processing, the performance of actors can be improved by providing cues that help highlight the occurrence of the activity's key events. Moreover, cues that encode information that help identify the type of event will provide additional performance gains.

Figure 14:
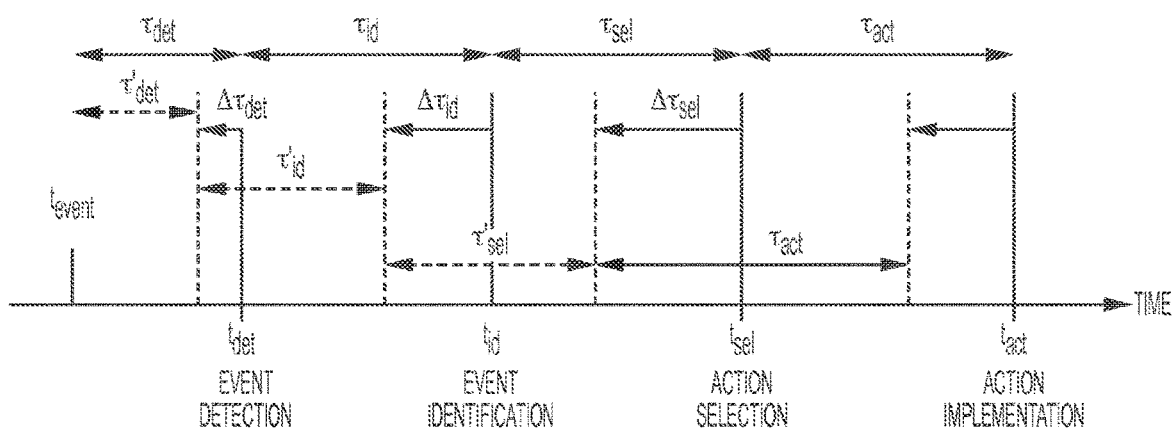
FIG. 14 describes the human information processing steps on a timeline with the detection time $\tau_{det}$, identification time $\tau_{id}$, the action selection time $\tau_{sel}$ and the action implementation $\tau_{act}$. The figure also highlights how cues assist in the detection reducing detection time to $\tau'_{det}$, identification $\tau'_{id}$ and selection $\tau'_{sel}$ of an action.

FIG. 14 describes the human information processing steps on a timeline with the detection time $\tau_{det}$, identification time $\tau_{id}$, the action selection time $\tau_{sel}$ and the action implementation $\tau_{act}$. The figure also highlights how cues assist in the detection process therefore reducing detection time $\Delta\tau_{det}$, as well as, identification $\Delta\tau_{id}$ and selection $\Delta\tau_{sel}$ of an action. These processes have to take place fast enough to sustain the speed of interactions of a game or activity.

For example, in tennis, the players learn to detect and identify racket stroke and player court motion. Their brain needs this information to predict the outcome of these events ("other" state) which in turn is used to determine and plan appropriate actions to implement. Moreover, timing cues, have additional beneficial effects on performance. Similar to those provided by metronome for musicians, timing cues help preserve the rhythmic pattern in the motor, perceptual and cognitive processes' cycles. These rhythmic characteristics of behavior are fundamental to the organization of the brain processes (see Buzsaki, Rhythms of the Brain, Oxford University Press, 2006).

The following sections describe example application to the tennis. It details the court and game events, the time scales of the interactions, the behavioral characteristics that represent the basis of the cueing, and the method of operation.

Many other activities can be described similarly and therefore will benefit from the cueing technology. Examples of other sport applications include team sports such as soccer, American football, basketball, etc. Professional teams increasingly use measurements for analysis and training. Cueing devices could be used to provide real-time instructions generated automatically from interaction models, the cueing system could also involve human inputs such as from coaches interacting with real-time analytics. An important and representative vocational example include the optimization of workflow in an operating room (so called context aware operating room). Measurement of the environment variables such as the procedure stage along with the team member states and behaviors can be processed to generate cues that enhance situational awareness and help anticipation the need for instruments, alert surgeons, surgical assistants, nurses, etc. The improved synchronization and coordination of the surgical team can reduce surgical time and errors (Padoy, "Statistical modeling and recognition of surgical workflow," Medical Image Analysis, 16(3), 632-641 (2012)).

Method of Operation Overview

Tennis encompasses a range of behaviors that need to be planned and organized based on the immediate interactions during the game and more deliberate decisions that depend on the game plan of each participant. Humans and animals are able to extract cues directly from their environment sensory interactions (Turvey, "The ecological approach to perceiving-acting: A pictorial essay," Acta Psychologica 63, no. 2: 133-155 (1986)). These so-called ecological cues are mostly used as direct guides to coordinate movement behavior. For example, the racket ball strike or the ball's ground contact are most likely ecological cues. There are also the subtler, higher-level cues that can help predict key outcomes such as provide information about the type of stroke the adversary is about to execute. Finally, advanced players also keep track of more abstract outcomes such as the patterns of play of the adversary.

The racket ball strike is relatively easy to extract from measurements since the impact of the ball on the racket produces multiple forms of physical effects. The impact manifests as an impulsive force acting on the racket and the ball, respectively. This impulse causes a change in both the racket and ball velocities. The force also causes the ball and the racket string bed to deform. Both of these changes can be detected using sensors on the rackets.

Timing and movement phases information can be obtained from the racket movement characteristics associated with the specific racket stroke phases. The most distinctive ones are: backswing where the player brings the racket back from the ready position; the forward swing initiation where the player imparts a forward acceleration on the racket; and the ball impact discussed previously. As mentioned earlier, advanced players are able to utilize early cues derived from the preparatory stroke motion.

Different measurements can be used to extract events used to generate cue signals. For example, an inertial sensor can be configured to provide the measurement necessary to detect the instant the racket strikes the ball for example by detecting the impulsive change in racket translational or rotational acceleration. Stroke preparation and initiation can be detected similarly.

Alternatively, an acoustic sensor could be used to provide the measurement needed to detect a change in air pressure resulting from the impulsive force accompanying the sound wave generated by the ball, string bed and racket frame deformations. Other measurements and detection techniques could be used: for example, detecting the racket or string bed deformation from strain gauge measurements or detecting the disturbance in the local light field caused by the ball movement as it approaches and leaves the racket from the signals obtained from an optical sensor. As will be appreciated by those skilled in the art one or more sensors can be mounted on the racket or incorporated in the racket or deployed on the environment (e.g., the tennis field). As will be appreciated by those skilled in the art, the optical sensor can be a single sensor or can be, for example, a camera system set-up in the environment which includes multiple sensors.

Figure 4:
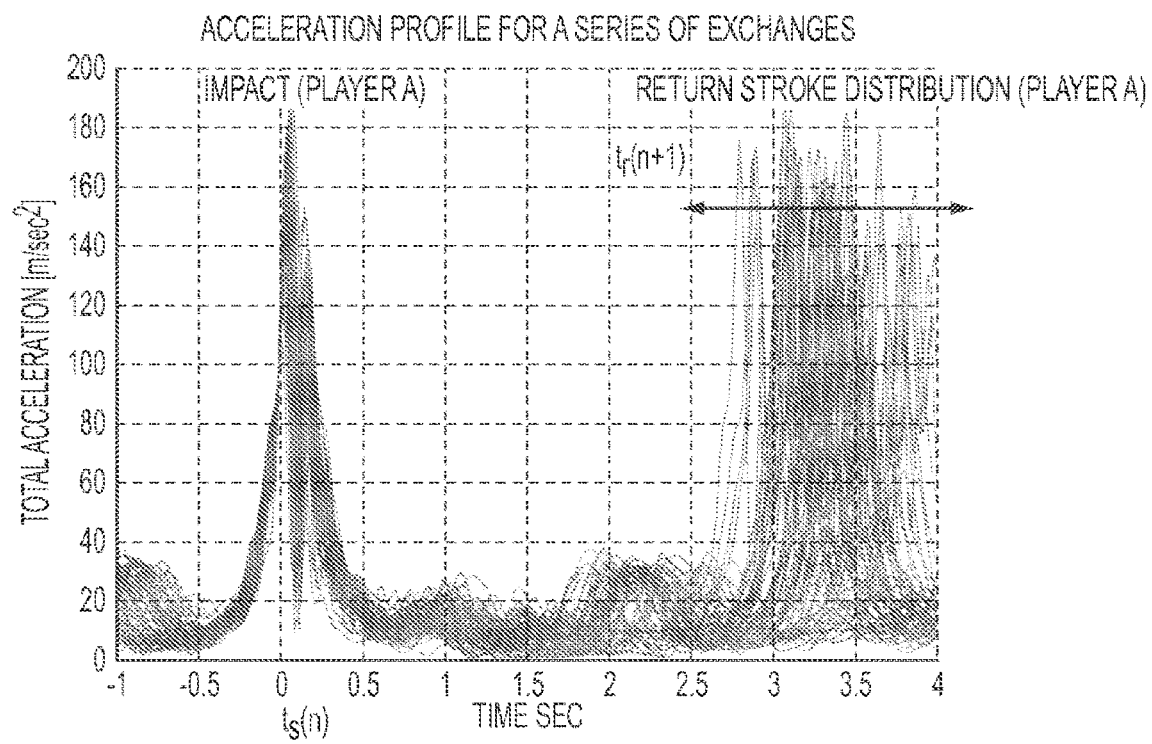
FIG. 4 illustrates an ensemble of acceleration profile for a player rackets' total acceleration. The figure highlights the distribution in duration for a total exchange return and the stereotypical characteristics of the acceleration profile. The total acceleration (in m/sec$^2$) from 0-200 m/sec$^2$ is shown over a period of time in seconds from −1 to 4. The impact for player A occurs at approximately time=0, while the return stroke for player A is typically between 2.5 and 4 seconds from the impact.
Figure 5:
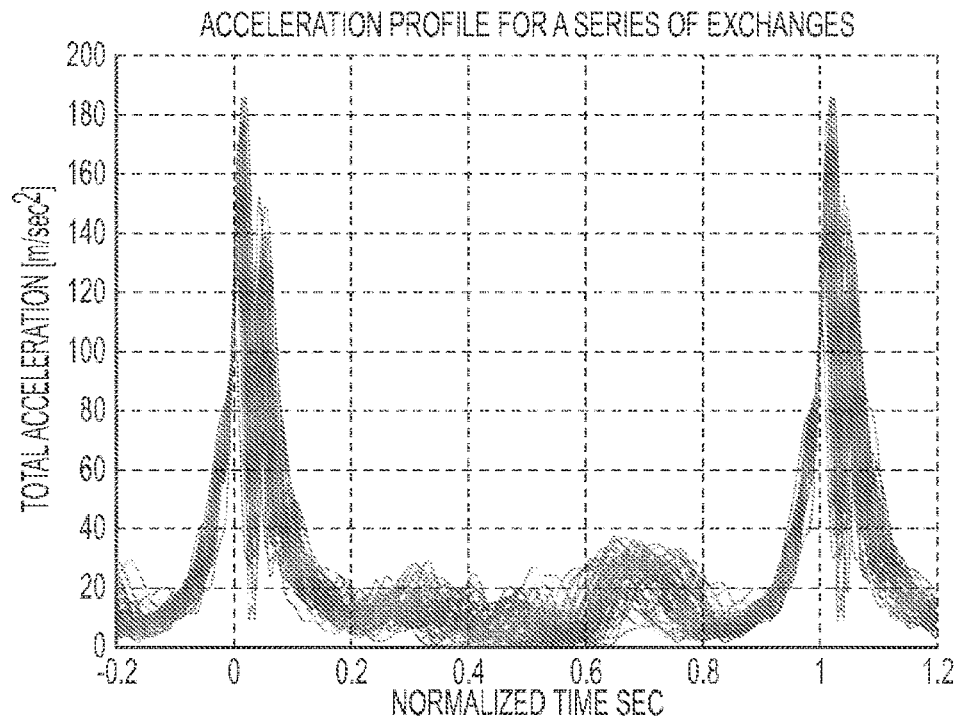
FIG. 5 illustrates an ensemble of time-normalized acceleration profile generate from FIG. 4. The normalization highlights the invariant timing characteristics that can be exploited in feature detection and extraction for the generation of a temporal cueing signal. The total acceleration from 0 to 200 m/sec$^2$ is shown against a normalized time in seconds from −0.2 to 1.2.

FIG. 4 and FIG. 5 show the patterns in total acceleration that can be observed in the time histories of that measurement for an ensemble of exchanges obtained from a racket mounted inertial measurement unit ("IMU"). Detection and extraction are possible using simple thresholds.

Figure 6:
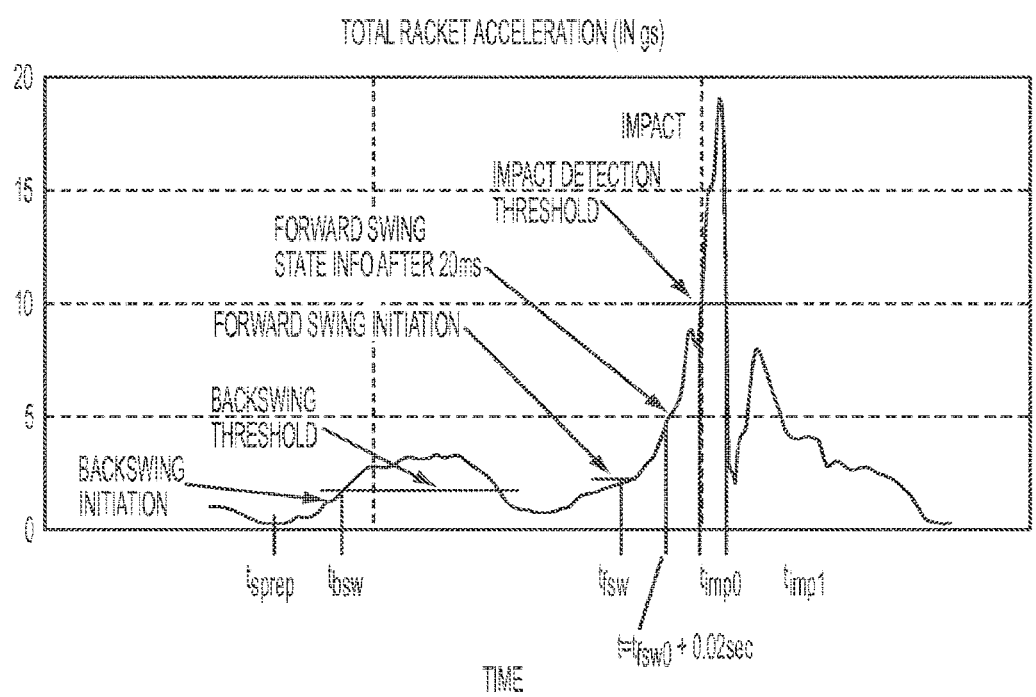
FIG. 6 illustrates the timing features available from total acceleration in g's with the thresholds used for their detection and extraction over a period of time. The features include: stroke backswing $t_{bsw}$, stroke forward swing initiation $t_{fsw}$, and stroke impact $t_{imp}$.

FIG. 6 depicts timing features available from total acceleration with the thresholds used for their detection and extraction. The time features include: stroke preparation $t_{sprep}$, stroke backswing initiation $t_{bsw}$, stroke forward swing initiation $t_{fsw}$, and stroke impact $t_{imp}$.

Alternatively, more general pattern recognition techniques could be implemented in a data driven fashion such as Hidden Markov Model (Rabiner, Lawrence R., "A tutorial on hidden Markov models and selected applications in speech recognition," Proceedings of the IEEE 77, no. 2: 257-286 (1989)). These techniques have the advantage that no prior knowledge about the patterns and structures are required.

Capturing the ball's ground strike and net crossing can be captured with court-based ball motion tracking systems such as the HAWK-EYE system available from Hawk-Eye Innovations Ltd. These systems can also provide the racket strike and stroke information. Other, temporarily mountable optical/sound sensor systems can be used and/or audio sensors to identify environment events timing and location such as net crossings and ground impacts (see FIG. 15).

Once the relevant events have been detected in the players and environment, the data have to be processed to produce cues. These then have to be communicated to the players where they will help initiate the stroke preparation, as well as trigger the various actions required for effective play including court movements and attending to additional cues necessary to fine tune the stroke.

The signal associated with the impact time or racket stroke initiation extracted at the instant of the stroke can be processed locally, centrally, or transmitted to the opponent's wearable or racket mounted device where it is transformed into a perceptual cue such as an audible, tactile, or visual stimulus or a combination thereof.

Figure 7:
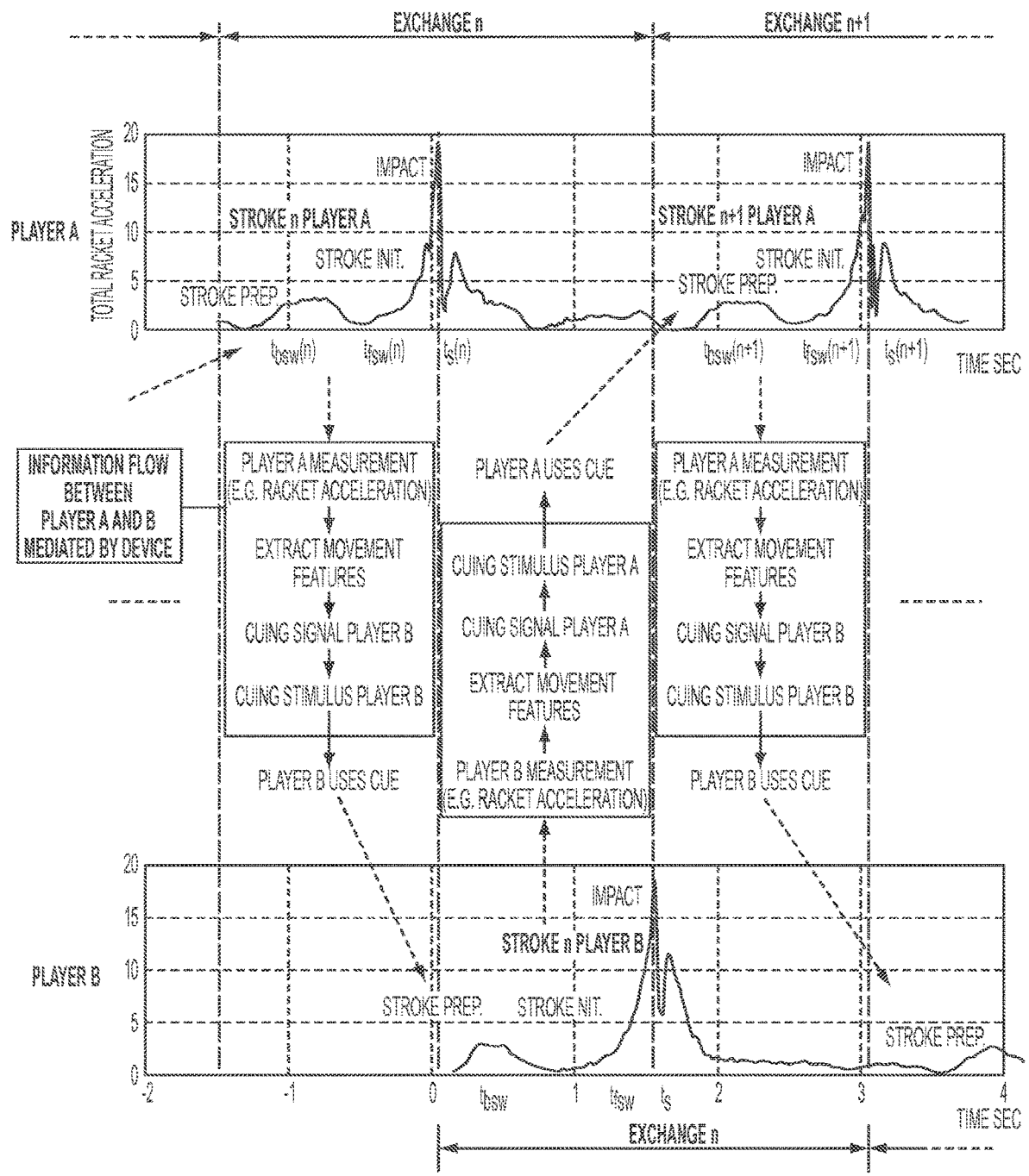
FIG. 7 illustrates the extracted timing features from a recorded total acceleration time history and how they are used as cueing signal during exchanges between two players A and B

FIG. 7 shows the extracted timing features from a recorded total acceleration time history and how they are used as cueing signal between two players A and B.

Figure 8:
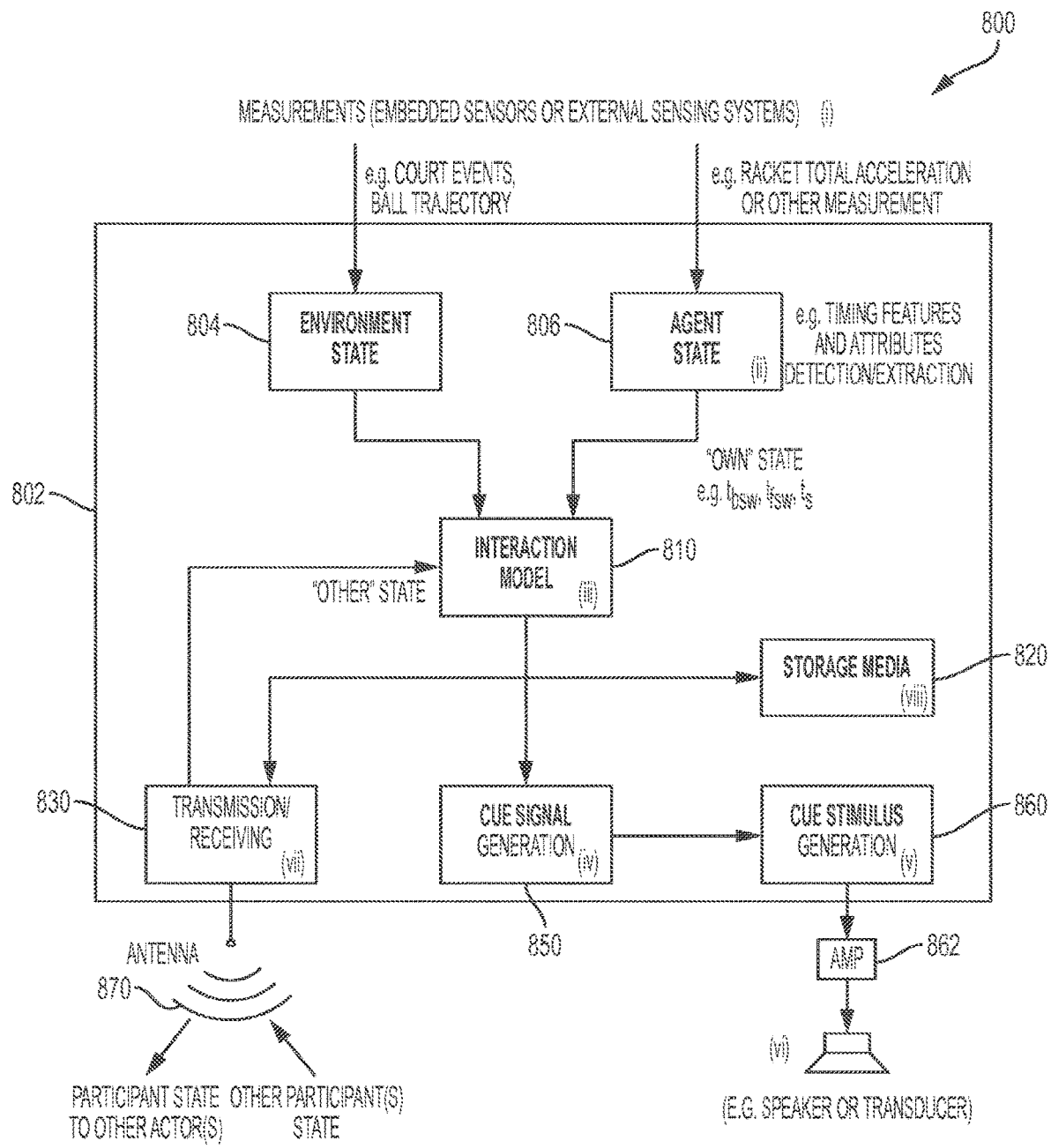
FIG. 8 is a system block diagram of a self-contained cueing device that implements components of the cueing system including acquisition of the user's measurements, state estimation of user behavior (timing feature detection and extraction), the cue signal generation, communication of cueing stimulus via a transducer (audible, haptic, or visual), wireless transmission and receiving of relevant states to and from the other users.

FIG. 8 is a system block diagram of the cueing system 800 of the processes used for the implementation of the cueing algorithm including the measurement, the timing feature detection and extraction, the cue signal generation, radio-transmitter for the transmission and receiving of the cueing signal to/from the other racket/player, and transducer to communicate a cueing stimulus (audible, haptic, or visual). The device 802 includes an environment state 804, an agent state 806 which feeds into an interaction model 810. A storage media 820 is also provided which is in communication with a transmission receiver 830. A cue signal generator 850 is provided along with a cue stimulus generator 860. An antenna 870 can be provided to communicate to other devices as well as an amplifier 862, such as a speaker or transducer.

Tennis Timing Codification and Notation System

A notation system can be designed to establish timing relationship between the relevant actors and environment events. The following example illustrates such a system for tennis player's movement behavior (including stroke as well as body movements such as footwork, etc.) and game events for each successive exchange. Such a system provides a formal basis for the analysis and modeling of the key interactions between actors and their task environment and the design of the cueing and feedback laws used for the interactive cueing system. In addition to the timing of the various events, state information can also be recorded including the positions of the players, orientations of the rackets, ball speed and spin (See FIG. 15). The choice of information depends on the available measurements and the desired level of analysis. For example, the direct cues including stroke impact require racket acceleration and simple modeling. In contrast cueing based on the pattern of play requires more comprehensive measurements and analysis of the game plans, etc.

An exchange between two or more players (e.g. B, shown in FIG. 2) is defined relative to one of the player's. For example, an exchange for player B in FIG. 2, corresponds to the time interval between the oncoming ball from the time of player A's stroke initiation, including player B's return strike of the same ball, up to but not including the instant of player A's subsequent impact of the same ball. The definition encompasses the full interaction that determines player B's behavior and effect on the environment (ball trajectory on the court). Here it is assumed that information before the opponent's stroke does not influence the subsequent behavior and stroke.

This system can also be used to generate post-game analysis for entertainment or training. Information collected during game play can be transmitted to a secondary device, such as a laptop or tablet, for further access.

Since it captures the interaction between the actors or players, the information can be used to analyze the quality of the players' interactions. This information could be used to pair players. The environment and actors' events in tennis correspond to: Court or game events that can typically be observed and objectively captured and measured. These include the ball's impact on the racket, the ball crossing the net and bouncing on the ground. Most of these events are described by the ball's spatial location with respect to the court. Player behavioral and stroke events. These combine internal perceptual and cognitive events, which cannot easily be measured and recorded, and more objective events encompassing body motion footwork and racket stroke.

Court or Game Events

For each exchange n consider the following events: Strike time $t_s(n)$; Net crossing time $t_n(n)$; Bounce time $t_b(n)$; and Return time $t_r(n)$=Impact time $t_s(n+1)$. If the player hits a volley then $t_b(n)=\{\emptyset\}$. In a match, the first impact of each game is a serve.

The sequence of court events can be arranged as a time series as follows:

$$T_{court} = \begin{bmatrix} t_s(n-1) & t_n(n-1) & t_b(n-1) & t_r(n-1) \\ t_s(n) & t_n(n) & t_b(n) & t_r(n) \\ t_s(n+1) & t_n(n+1) & t_b(n+1) & t_r(n+1) \end{bmatrix} \quad (1)$$

Note that using the temporal events, other relevant time series can be computed including exchange duration from player A to player B: $T_e(n)=t_r(n)-t_s(n)$. This time series can be used to extract relevant timing statistics associated with the player behavior and interactions.

Player Behavioral and Stroke Events

The perceptual response time $t_{presp}$ for the opponent's return is defined as the duration between strike/return and its perceptual recognition:

$$T_{presp}(n) = t_{presp}(n) - t_s(n) = t_{presp}(n) - t_r(n-1) \quad (2)$$

The perceptual response time depends on several factors including the player's attention and perceptual skills. The player's goal is to have the smallest perceptual response time since it leaves more time to elaborate a plan and to prepare the stroke and court positioning.

Regarding the tennis stroke and its execution, the following actions are typically considered: beginning of forward swing; maximum trunk angular velocity; ball impact; and end of forward swing. (See Landlinger, "Key factors and timing patterns in the tennis forehand of different skill levels," J. Sports Sci. & Med. 9(4): 643 (2010)).

All of these actions, except for the pelvis and trunk angular velocities are determinable from racket kinematics. More comprehensive instrumentation could be used if these events want to be included in the analysis and cueing laws. FIG. 2 shows a timeline of the court or game events combined with the player's behavioral events.

Orders of Magnitudes of Tennis Timing

To comprehend how to best implement a cueing system, it is necessary to consider the key temporal dimensions in human physiology and their relationship to tennis stroke timings.

In the context of tennis, an event like the racket-ball impact is not a simple visual stimuli but rather a pattern of visual phenomena superposed with an auditory stimulus. To identify the event the brain combines visual pattern recognition with auditory recognition.

Sound travel time visual and auditory recognition involves a tradeoff between the near instantaneous travel time for light but finite for sound. The time it takes the sound of the impact to travel across the court from baseline to baseline is about $t_{sound} \approx 70$ msec (based on a distance of 23.78 m and sea level speed of sound $v_{sound}=340.29$ m/sec). Depending on the players' positioning this time will be somewhere in the range 30 msec$<t_{sound}<$90 msec. Interestingly, the sound travel time is large enough to take away the physiological advantage of auditory response time over visual.

Ball travel time Medium to fast ball speeds range between about 20 and 40 m/sec. SEELEY, "Tennis forehand kinematics change as post-impact ball speed is altered," Sports Biomech. 10(4): 415-426 (2011). These values are on average about one tenth of the speed of sound therefore the ball travel time is approximately in the range $0.3<t_{ball}<2$ sec.

Stroke timing for an elite player's forehand with respect to the impact time is shown in Table 1.

TABLE 1

STROKE TIMING

| | |
|---|---|
| −0.26 sec | Forward swing initiation |
| −0.075 sec | Maximum pelvis angular velocity |
| −0.057 sec | Maximum trunk angular velocity |
| 0 sec | Ball impact |
| +0.06 sec | End of swing (forward motion) |

Landlinger, "Key factors and timing patterns in the tennis forehand of different skill levels," J. Sports Sci. & Med. 9(4): 643 (2010).

The timing of critical actions and events span a range of duration from about 30 msec to 2 sec. Table 2 illustrates timing amounts for a range of actions.

TABLE 2

TIMING ORDERS OF MAGNITUDE

| | |
|---|---|
| 30-90 msec | Sound's travel time |
| 0.14-0.2 sec | Ideal reaction times |
| 0.2-0.4 sec | Stroke initiation to ball impact |
| 0.3-2 sec | Ball's travel time btw player and opponent |

The major stroke events manifest clearly in the total acceleration measurements. FIG. 6 shows an example of timing features directly available from total acceleration with the thresholds used for their detection and extraction. The features include: stroke preparation $t_{sprep}$, stroke backswing initiation $t_{bsw}$, stroke forward swing initiation $t_{fsw}$, and stroke impact $t_s$. More subtle events can be detected from features that combine components of the racket acceleration angular rates. These event, as mentioned earlier, and their interaction can also be determined from pattern analysis or statistical modeling techniques.

Codification of the Combined Game and Player Events

For a more comprehensive description of timing of key actions and interactions, the following considers some of the relationships between the player/stroke events and game events (see FIG. 2).

The perceptual response time $T_{presp}$ is defined as the duration between the ball impact (the stimulus) and the perceptual response:

$$T_{presp}(n) = t_{presp}(n) - t_s(n)$$

It provides a measure of the perceptual fitness. The perceptual response is difficult to directly measure. It could be estimated using a gaze tracking system, however, covert attention does not necessarily involve eye motion. The motor reaction time $T_{mreact}$ is defined as the duration between the perceptual response and the actual onset of a motor response, e.g., court movement or stroke preparation:

$$T_{mreact}(n) = t_{mreact}(n) - t_{presp}(n) \qquad (3)$$

The preparation margin $T_{pmarg}$ is defined as the duration between the motor response and the stroke preparation:

$$T_{pmarg}(n) = t_{sprep}(n) - t_{mreact}(n)$$

It provides a measure of the preparation time following the motor response and provides a measure of physical fitness and agility.

The stroke margin $T_{smarg}$ is defined as the duration between the stroke preparation and the stroke backswing initiation:

$$T_{smarg}(n) = t_{bsw}(n) - t_{sprep}(n) \qquad (4)$$

It provides a measure of available time margin between the state of optimal readiness and the actual stroke initiation. A larger stroke margin indicates that a player has extra time that could be used for example to optimize their preparation.

The stroke time $T_{stroke}$ is defined as the time between backswing initiation $t_{bsw}$ and the return or strike time:

$$T_{stroke}(n) = t_r(n) - t_{bsw}(n) \qquad (5)$$

In addition, other event times relating to court and behavioral events can be defined, including, the bounce-return time $T_{br}$:

$$T_{br}(n) = t_r(n) - t_b(n) \qquad (6)$$

Similarly, the bounce-backswing initiation $T_{bbsw}$:

$$T_{bbsw}(n) = t_{bsw}(n) - t_b(n) \qquad (7)$$

Or, similarly the bounce-forward swing initiation $T_{bfsw}$:

$$T_{bfsw}(n) = t_{fsw}(n) - t_b(n) \qquad (8)$$

Both of these are believed to be key quantities for stroke timing. They describe how the two primary stroke initiation phases are related to the ball ground contact, which is sometimes considered a cue for triggering the stroke motion.

Combining the court and behavioral events:

$$T_{behav} = \begin{bmatrix} t_s(0) & t_{presp}(0) & t_{mreact}(0) & t_{sresp}(0) & t_{bsw}(0) & t_{fsw}(0) & t_n(0) & t_b(0) & t_r(0) \\ \vdots & \vdots & \vdots & \vdots & \vdots & \vdots & \vdots & \vdots & \vdots \\ t_s(n-1) & t_{presp}(n-1) & t_{mreact}(n-1) & t_{sresp}(n-1) & t_{bsw}(n-1) & t_{fsw}(n-1) & t_n(n-1) & t_b(n-1) & t_r(n-1) \\ t_s(n) & t_{presp}(n) & t_{mreact}(n) & t_{sresp}(n) & t_{bsw}(n) & t_{fsw}(n) & t_n(n) & t_b(n) & t_r(n) \\ t_s(n+1) & t_{presp}(n+1) & t_{mreact}(n+1) & t_{sresp}(n+1) & t_{bsw}(n+1) & t_{fsw}(n+1) & t_n(n+1) & t_b(n+1) & t_r(n+1) \\ \vdots & \vdots & \vdots & \vdots & \vdots & \vdots & \vdots & \vdots & \vdots \\ t_s(N_k) & t_{presp}(N_k) & t_{mreact}(N_k) & t_{sresp}(N_k) & t_{bsw}(N_k) & t_{fsw}(N_k) & t_n(N_k) & t_b(N_k) & t_r(N_k) \end{bmatrix} \qquad (9)$$

where $N_k$ is the number of exchanges in the k-th rally.

The key temporal parameters can be obtained from these quantities by simple difference:

$$T = \begin{bmatrix} T_{presp} & T_{mreact} & T_{pmarg} & T_{smarg} & T_{stroke} & T_{nr} & T_{br} & T_{bbsw} & T_{bfsw} \end{bmatrix}' = \begin{bmatrix} -1 & 1 & 0 & 0 & 0 & 0 & 0 & 0 & 0 \\ 0 & -1 & 1 & 0 & 0 & 0 & 0 & 0 & 0 \\ 0 & 0 & -1 & 1 & 0 & 0 & 0 & 0 & 0 \\ 0 & -1 & 0 & 1 & 0 & 0 & 0 & 0 & 0 \\ 0 & 0 & 0 & 0 & -1 & 0 & 0 & 0 & 1 \\ 0 & 0 & 0 & 0 & 0 & 0 & -1 & 0 & 1 \\ 0 & 0 & 0 & 0 & 0 & 0 & 0 & -1 & 1 \\ 0 & 0 & 0 & 0 & 1 & 0 & 0 & -1 & 0 \\ 0 & 0 & 0 & 0 & 0 & 1 & 0 & -1 & 0 \end{bmatrix} T_{behav} \quad (10)$$

Each of these are vectors of time series from the first exchange in a rally (or point in a game) n=1 to the last exchange $n=N_k$. Note that this is not a comprehensive list. Additional quantities can be formed depending on the available measurements and the level of analysis. For example using a gaze tracking system it would be possible to define quantities such as the time interval between the instant the gaze intercepts the ball and the forward swing initiation.

Foundations for Cueing

Effective play relics on the execution of a sequence of coordinated actions. These actions rely on preparatoly actions such as court positioning and stroke preparation. One player's preparatory actions are based on cues extracted from the various behavior of the other player including court motion, body stance, racket motion, eye motion, etc. As discussed in the introduction, the racket's ball strike is considered to be a primary event since it conveys high-quality cue about the timing of the returning trajectory. Furthermore, the intensity of the strike provides information about the pace of the oncoming ball.

The perceptual reaction time $T_{presp}$, motor reaction time $T_{mreact}$, stroke preparation time $T_{sprep}$ and stroke execution $T_{stroke}$ cannot be reduced arbitrarily for a given skill level since they depend largely on preprogrammed neuro-motor processes and muscular responses. They can be improved through training or through the action of augmentations.

Cueing can be conceived based on the human information processing model (FIG. 13) and therefore has three major modes of action, which are to facilitate: event detection, event identification and action selection. Where two tennis players are engaged in a rally, over a period of time each player engages in a series of actions: ready/waiting, backswing, forward swing, follow through, impact, and follow through end.

Figure 11:
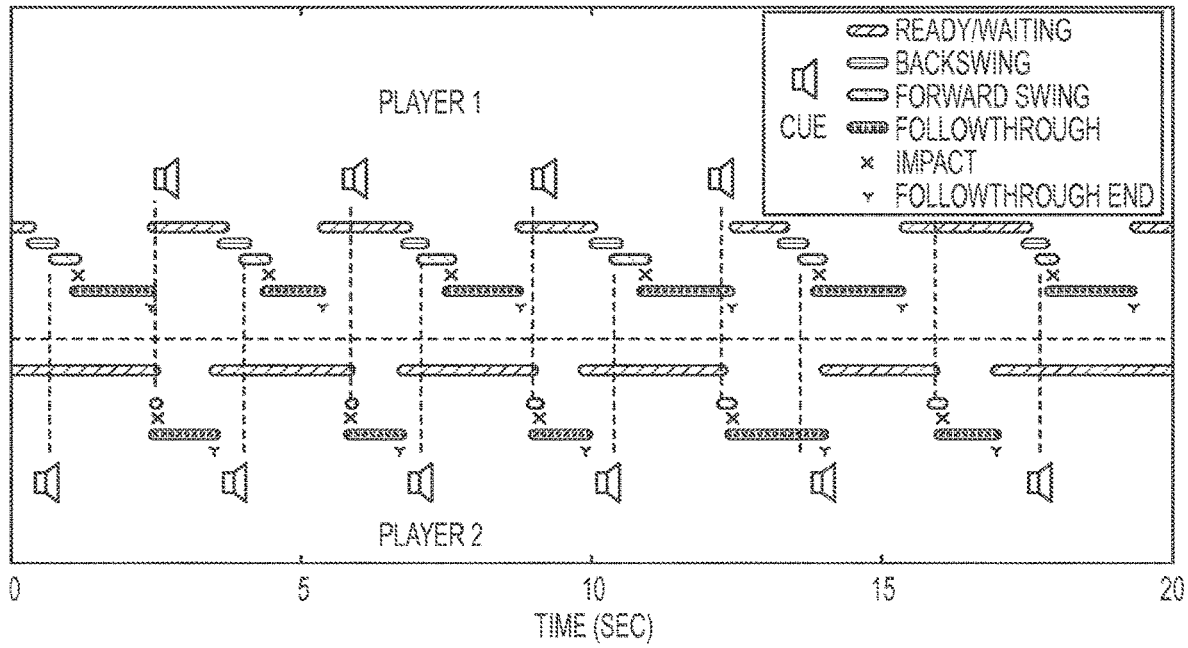
FIG. 11 illustrates the traces of finite-state estimation from two tennis players engaged in a rally.

The traces of finite-state estimation from two tennis players engaged in a rally are shown in FIG. 11. Additionally, administration of exemplar cues at a time to either player is also illustrated along the timeline.

Figure 12:
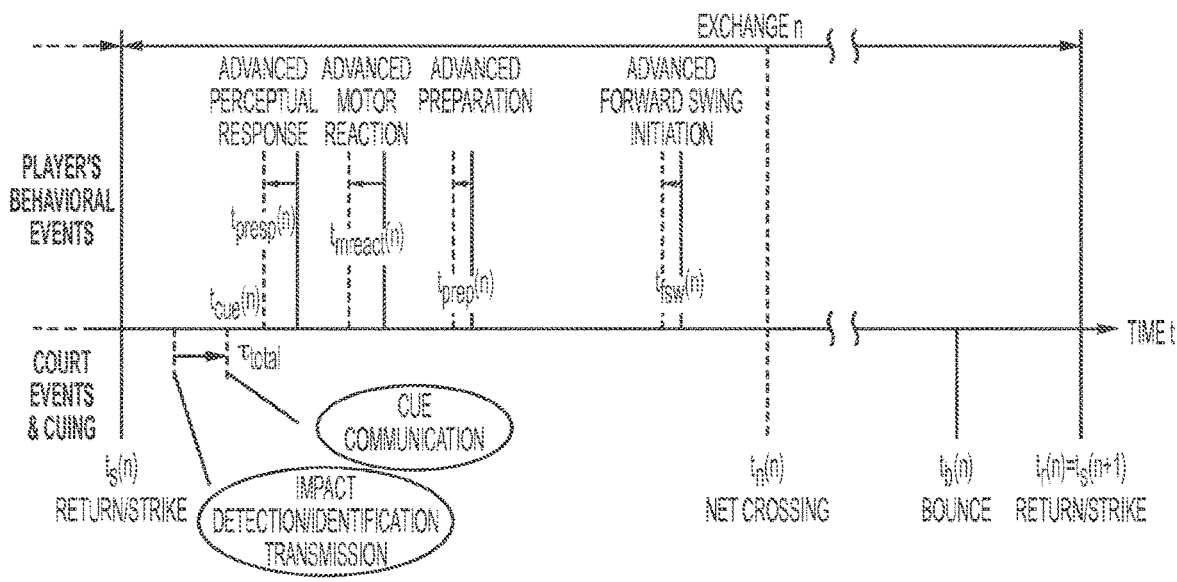
FIG. 12 illustrates the effects of a cue on the perceptual response and selection and preparation of appropriate movement response in tennis.

The effect of the first level of cueing is to reduce the perceptual response time $t_{presp}$ (time between the opponent's strike or return and the recognition of that event). The cue enables an earlier detection of the event, which will result in a net increase in the time available for event identification, action selection, preparation (see FIG. 12).

The second level, enabled by encoding information about the event type in the cue, will further increase the available time since the actor does not need to perform the additional processing required for the event identification. Assuming the actor has trained the response selection based on the event, the cue will trigger the action, e.g. selection of a specific type of stroke. By reducing the range of event it will reduce the time (see choice reaction time).

Finally, the third level, action selection, is enabled by encoding information about the type of action that should be ideally selected given an identified event. This level of cueing could in theory supplant all the human perceptual and decision making tasks from the actor who can then focus on the correct execution of the action (e.g. assume the correct body posture and focus on the initiating and execution associated with the selected stroke type).

These various forms of cueing can also act as reinforcement during training and therefore are going to help the formation and consolidation of the processes associated with the event detection, identification and action selection. The temporal quantities used for cueing depend on available measurements. The information needed to implement temporal cueing can be obtained from a variety of sensing systems or modalities.

Method of Operation

The quantities in the determination of cueing actions depend on available measurements. The information needed to implement cueing can be obtained from a variety of sensing systems or modalities:

Court-based vision or optical based ball tracking system such as HAWK-EYE that provides ball location and trajectory relative to the court. These data can be processed to extract the court event data including the net crossing or court ground impact, as well as, player events data including racket impact. Court-based acoustic measurement system such as sonar or simpler microphone-based devices. Sensors on a racket used to detect racket strikes using a variety of sensing methods including for example racket acceleration or string-bed and racket frame strain. Racket mounted or integrated sensors used to detect and estimate stroke event such as the time and magnitude of the forward swing and the time and magnitude of impact with the ball (FIG. 4). These modalities could also be combined.

The following description of the method of operation focuses on a use case where racket stroke characteristics and racket-ball strike data are the primary signals used for cueing. The most basic, or minimal, implementation would involve detection of the racket change in linear and/or angular momentum at ball strikes and racket backswing and forward swing movement characteristics. These features can be obtained from a racket mounted inertial acceleration and angular rate sensor such as provided by a micro-electronic-mechanical-system (MEMS) inertial measurement unit (IMU).

Note that similar information necessary for cueing could be obtained from a centralized measurement system such as HAWK-EYE. Measurement therefore should be understood as any quantitative form of a signal obtained from a system of observation of the game elements, including but not limited to ball and racket trajectory.

General Setup

FIG. 15 shows key outcomes of player A's stroke on the environment (court event and ball trajectory). The figure illustrates the cueing process relating player A's behavior, the outcome player B's state and the cue produced for player B. The figure focuses on the longitudinal/vertical trajectory outcome. Players' behavior are described by the stroke movement and impact location, the environment is described by the ball trajectory and velocity. Together these variables determine the resulting ball trajectory. For example, depending on player A's stroke (stroke type and magnitude), the ball velocity, height, and longitudinal location at impact the returning ball trajectory can follow a variety of longitudinal profiles. For example, a flat (FL) or a top spin (TS) stroke will result in different trajectory shapes (shown here in terms of the next clearance and ball depth or baseline clearance) as well as ball velocities at ground contact (speed of the ball and incidence of the velocity before and after the bounce). The measurement of player A's stroke and the racket state at impact can be used to predict the ball trajectory. This information can then be used to cue player B, for example producing a cue stimulus that encodes expected ball velocity and spin type. This information in turn will help player B by providing anticipatory identification and action selection (see information processing model FIGS. 13 and 14).

The devices can be formed integrally in the racket frame itself or fitted on an existing racket frame or its string bed using a suitable securement device 310. Additionally, devices can, in some configurations, be wearable.

Figure 3A:
FIGS. 3A-3C illustrate a racket mounted cueing device that can be strapped onto a racket. The device shown is self-contained incorporating sensors necessary for obtaining relevant measurements, processor for the stroke detection, extraction and implementation of the cueing algorithm, radio-transmitter for the communication of the cueing signal to the other racket, and transducer for the generation of an audible, haptic or visual cueing stimulus.
Figure 3B:
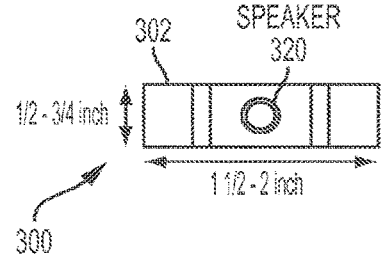
Figure 3C:
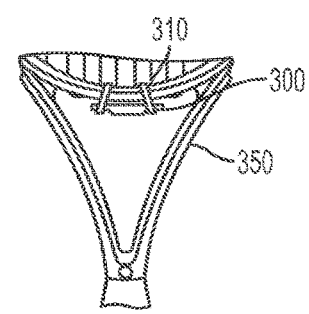

FIGS. 3A-3C illustrate detection and cueing device 300 affixed near the throat of a racket 350 where the cueing device 300 will be close enough to a player's ears following the stroke recovery for the player to perceive any cue. The racket throat typically also represents the section used to hold the racket by the non-dominant hand which is ideal if a combination of haptic and auditory signaling is considered. The device 300 has a housing 302 which contains, the example, one or more sensors, logic, cueing devices, and a power supply. Suitable cueing devices can be, for example, speakers, vibrating generators, etc. the device 300 can be incorporated into the racket 350 or affixed via a suitable securement feature 310. The securement device 310 can be any suitable device for securing the cueing device to, for example, the racket. Suitable securement devices include, but are not limited to bands, straps, screws, and bolts. One or more sensors are included and one or more cue administrators (such as speaker 320) are also provided.

Note that various other configurations for the device components and functionalities are possible. For example, cueing signal could be provided by an accessory device attached to equipment, body, clothing, etc. The cueing device may also communicate to eyeglasses or smart watch, etc.

The device is affixed on each player's racket (e.g. player A and player B). During an exchange between players A and B, the backswing initiation, forward swing initiation and impact times are detected and extracted by the devices along with their signal attributes (e.g. forward swing acceleration and impact strength). These quantities are instantaneously communicated from the player striking the ball (e.g. A) to the device of the player who will be returning the ball next (e.g. B). Player B receives a cue stimulus or stimuli (auditory, visual, or haptic) based on the extracted stroke features. Player B uses these cues to best prepare and initiate the stroke.

FIG. 7 shows the extracted timing features from a recorded total acceleration time history and their integration between the two players, Player A and Player B.

FIG. 8 shows a block diagram illustrating the cueing processes that could be used for a racket-integrated implementation:

(i) Measurements of racket motion from sensor integrated on the device are generated during the play as well as measurements from the court events and other player behavior.

(ii) An algorithm estimates the actor's own state for example detects and extracts relevant stroke timing features and their attributes (for example the time and strength of the impact). In parallel another (by applying an) algorithm may be used to estimate the environment state data collected by one or more sensors.

(iii) The actor's state and environment state are combined to determine the interactions and outcomes relevant to the activity.

(iv) The data is used to synthesize a cue signal.

(v) The cue signals are used to generate a cue stimulus.

(vi) The cue stimulus is amplified and relayed to the transducer where it is transformed in an auditory, haptic or visual cue stimulus.

(vii) The relevant state data are transmitted through a radio-transmitter to the second player's device (player B).

(viii) The measurement, timing features and cue signals, etc. can be recorded on a storage media.

The player perceives the cue stimulus which triggers a behavioral response such as a body movement and stroke preparation. The timing and magnitude information encoded by the stimulus support variable responses based on the opponent's behavior and hence provide information to best anticipate the oncoming ball.

Cue Stimuli Forms

The temporal signals such as stimulus impulses alone are relevant for cueing. However, these basic temporal cue stimuli can be augmented using relevant attributes such as the magnitude of the impact or stroke initiation, or outcome information such as ball direction or amount topspin. These attributes can be embedded in the cue signal through amplitude, frequency or phase modulation. In addition, the cue signals from both players can be combined to form interactive cue signals. The best form of cue requires taking into account ecological perceptual and behavioral factors. For example, tau theory which considers the perceptual signal for the coordination of body movement. Lee, D. N., "Guiding movement by coupling taus," Ecological Psychology, 10(3-4) 221-250 (1998).

The following describes different cueing forms that can be implemented starting with the most basic impact temporal cue to more advanced cue signal modulation, interactive cue signals and cue patterns.

Basic Cue Stimuli Features

The basic cueing consists in sending the receiving player a "temporal" cue stimulus following the instant the striker's racket hits the ball. The stimulus can be audible, haptic, and/or visual (such as in heads-up eye glass display) or a combination. Since it can take less than one second for the ball to travel across the court, the signal has to be generated and transmitted within a few of tens milliseconds of detection to be effective as a cue.

Enhanced basic cueing consists in sending the receiving player a "temporal" cue stimulus following "anticipatory" stroke events such as instant the striker's device detects stroke preparation or stroke initiation action.

For example, extracting and communicating a train of cue stimuli that coincide with the stroke backswing, forward swing initiations and impact would provide a relatively complete "image" of the stroke which the players would learn to use to predict the type of return to expect. The stimuli could be modulated in volume or tone to encode intensity of the associated stroke phases.

The stroke events can also be combined to generate a composite temporal cue stimulus.

Advanced Cue Stimuli Features

More advanced cueing features can be implemented by modulating, phase shifting, or augmenting the cueing signals. The magnitude and frequency of the cueing stimulus can be modulated based on the magnitude of the strike. This allows providing the player with anticipatory information about the speed of the ball or other relevant characteristics.

The cue signal can also be delayed by a variable duration. The nominal delay would correspond to some nominal stroke intensity and the delay would be advanced or delayed based on stroke intensity. This allows providing the player with anticipatory information about the speed of the ball.

Interactive Cue Stimuli Patterns

The cueing signal can also be conceived as a pattern. The pattern consists of a cue signal train augmented with intermediate cue signal distributed at particular time intervals. In the simplest form consider the frequency of the strike interval:

$$f_1 = \frac{1}{[t_s(n) - t_s(n-1)]} \qquad (11)$$

The base frequency $f_1$ can be used to generate cue signals of higher harmonics such as $f_2=2f_1$ to help maintain regular timing. The cue signal can also be used to generate rhythmic signal pattern to help train particular play patterns. For example, in a groundstroke exchanges, the pattern can be adjusted based on the desired pace of the exchange. The pattern can also adapt automatically based on actual performance of the players as identified from extracted timing features. A typical example is to provide a timing cue following the impact to help the player bring the racket in the ready pose. The cue signal can be based on the combination of signals from the two players. For example, stroke initiation signal detected from the adversary's racket motion can be combined with the returning player's stroke preparation signal. The phase difference between the two signals provides a measure of advance or delay in the player's preparation and can therefore be used to modulate the cue stimulus.

Additional timing cues based on the game environment such as the balls ground strike of the ball or the net crossing could be inserted to help prepare and time the stroke. This is essential to enable early contact with the ball such striking it on the rise following the bounce. These court based event cues would typically require measurement about the ball's global trajectory or specific event detectors (e.g. as provided by acoustic or vision based devices). It would also be possible to predict the ball's trajectory relative to the court (including bounce location and time) from estimation of the player's position (obtained from the racket mounted device and other wearable sensors) and the model of the stroke outcome (see FIG. 9).

Other Capabilities

Devices can be used individually or paired with a device fitted on shoes or other body parts. When used individually the device provides a rhythmic cue, i.e. acting as a pacer, based on the ball's impact. For example, it can generate a timing cue at constant intervals following the impact. This interval can be user adjustable or adaptive based on stroke intensity. When paired with other device such as on the shoes it provides additional timing for footwork coordination. The technology and codification system can be used to provide game analysis. All the relevant data can be recorded and analyzed to provide temporal characteristics of player performance, game and stroke organization encompassing individual payer or about the particular patterns of interactions between the players.

Hardware Implementation

The temporal cueing system uses four primary processes:
1. Detection/extraction of movement events or phases.
2. Prediction of the movement outcome.
3. Processing of movement information to generate cue signal.
4. Communication of cue stimulus to player.

The device is configurable for one or more of the following:

Sensor for the detection of the impact of the ball on the racket (acoustic, vibration, inertial acceleration, angular rate, electromagnetic, optical, etc.).

Processor for the implementation of the cueing algorithm.

Radio transmitter for the communication of data between devices.

Pairing mechanism to prevent interference.

Transducer to generate perceivable stimulus (acoustic, haptic or visual).

The components can be in a single housing adapted to attach to an existing racket, or can be built into the racket, or a combination thereof where some components are built into the racket (e.g. sensors) while others are located in a separate housing (e.g. speakers). Some of the measurement, processing and signaling components can also be distributed between the racket, player and the ground or even be part of a cloud-based network.

Detection/Extraction of Temporal Cues

The detection of stroke phase events relies on the fact that stroke behavior exhibits several invariant features associated with key stroke phases. The most prominent ones are: backswing initiation, forward swing initiation, and impact. These features manifest in measurements such as obtained from the acceleration measurements or angular rates from an IMU.

FIG. 5 shows the total acceleration from a racket mounted IMU for a series of exchange intervals. As can be seen the general acceleration profile repeatable features associated with these key racket stroke phases.

Characteristic traits of these features can be used to identify and extract the associated temporal and state information. The impact is characterized by the impulsive acceleration. Therefore, the impact time can be extracted from the acceleration measurement by detecting when the acceleration exceeds a particular threshold value and drops below that threshold. For the stroke n, these times are denoted by the symbols $t_0(n)$ and $t_1(n)$. Other thresholds can be used to detect the stroke initiation and the preparation, respectively.

The features manifesting in the measurement for each phase is dictated by the laws of mechanics. Therefore, the measurements provide information that can be used to predict the future ball and/or racket trajectory and hence relevant for cueing the adversary. The following describes highly simplified racket-ball impact mechanics.

The ball's impact on the racket's string bed produces an impulse on the racket frame. This impulse is equal and opposite to the impulse experienced by the ball (Newton's second Law). The impulse experienced by the racket causes a change in racket momentum:

$$I_r(n) = \bar{F}(n)\Delta t(n) = m_r v_r(t_1(n)) - m_r v_r(t_0(n)) = m_r \Delta v_r \qquad (12)$$

where $\bar{F}$ is the average force during the duration of the impact $\Delta t(n) = t_1(n) - t_0(n)$. During the time of impact, it can be assumed that the total momentum of the system encompassing racket and ball is unchanged, therefore, the impulse acting on the ball is equal and opposite to the impulse acting on the racket:

$$I_r(n) = -I_b(n) = -\bar{F}(n)\Delta t = m_b v_b(t_1(n)) - m_b v_b(t_0(n)) = -m_b \Delta v_b \quad (13)$$

The ball's momentum change can in turn be used to predict the ball trajectory.

Note that ball trajectory predictions also require taking into account its angular motion (spin), and the aerodynamic forces (mostly drag and Magnus effect).

The magnitude of the racket (or ball) impact can be determined from the acceleration and angular rate measured by a racket-mounted IMU. For example, the racket's linear impulse is:

$$I_r(n) = \bar{F}(n)\Delta t = \frac{1}{\Delta t(n)} \left[ \int_{t_0}^{t_1} F(t)dt \right] \Delta t(n) = m_r \int_{t_0}^{t_1} a(t)dt \quad (14)$$

The impact time, can be taken as the mid-point of the impact time interval:

$$t_{strike}(n) = t_0(n) + \frac{(t_1(n) - t_0(n))}{2} = t_0(n) + \frac{\Delta t(n)}{2} \quad (15)$$

The racket stroke motion typically follows are well defined architecture. The stroke backswing involves a rapid step-like backward acceleration. The resulting pulse-like acceleration profile can be used to detect the stroke backswing initiation time and magnitude. The backswing magnitude could be approximated from the integral of the acceleration in the pulse region.

The stroke forward swing initiation involves rapid forward racket acceleration that culminates with the ball impact. The resulting continuous acceleration blends with the impulsive acceleration caused by the impact. The stroke forward swing initiation can be detected from the time when the acceleration exceeds a first acceleration threshold. The stroke forward swing initiation magnitude can be approximated by the integral of the acceleration from the end of the pulse to the initiation threshold.

Other detection techniques, tailored to the stroke architecture and impact, and their manifestation in the various forms of measurements (e.g. racket's angular rate components) can be used to extract cues.

The impulse $I_r$ also produces a deformation of the ball, string bed and frame. These physical processes, therefore, could also be used to detect the impact time and magnitude. The string bed and frame deformations can be measured by strain sensors on the frame or strings themselves.

In addition, the string bed, frame and ball deformations produce a local air pressure change which propagates as a sound wave. Therefore, the instant of racket-ball impacts can be detected by pressure or acoustic sensors. The ball's ground impact can be detected similarly.

Finally, other feature detection and extraction techniques could also be used to detect and extract relevant timing features that are not necessarily explicitly associated with the stroke and ball impact mechanics such as based on statistical pattern theory. For example, during exchange it could be possible to use statistical analysis between the two player measurements and court events and use this analysis to model these interactions and determine an optimal cueing model.

Processing of Timing Signal and Cue Generation

Given extracted features, these need to be processed and communicated to the players. The extracted data can be used to generate cue signals and cue stimuli in a variety of ways.

Simple Cueing

The most basic cue is achieved by communicating timing information, i.e., a signal coinciding with the adversary's behavioral events such as stroke preparation and/or initiation and/or racket-ball strike. These cues would alert the player to seek additional information such as precise ball trajectory, as well as, provide an objective temporal signal to prepare his/her stroke and court motion. As discussed elsewhere, the effectiveness of the cueing also is due to its nature as objective timing reference. Therefore, it is expected that communicating and signaling the instant of impact will help recruit the various perceptual, motor and cognitive processes and help prepare stroke and court motion. Finally, similar to a metronome, it can help establish a rhythm for the player.

Higher-Level Cueing

The next level of cueing involves encoding additional information that enable identification and response selection (see information processing model in FIG. 13). For example, the racquet-ball impact's impulse magnitude could be used to modulate the cue signal. A large impulse is related to large change in the ball's momentum, which means an increase in its speed. The magnitude cue therefore can help the player anticipate a faster ball.

This also raises a question about how the various pieces of information are encoded in the cue such that the player can easily perceive and then decode this information. The present example focuses on audible stimuli and therefore the information is primarily encoded in terms of the timing, amplitude and frequency modulation.

Temporal modulation. The cue could nominally be relayed as soon as it can be extracted, processed and communicated. Therefore, the earliest it can be available to the player is after a total delay:

$$\tau_{total} = \tau_{ext} + \tau_{proc} + \tau_{com} \quad (16)$$

Given the small time scales in sports such as tennis (see Tables 1 and 2), the total delay should ideally not be larger than a few milliseconds, e.g., less than 5-10 msec.

The basic implementation is to communicate the timing cue as soon as possible. Alternatively, the cue would be communicated with a small nominal delay that can be varied based on the impulse magnitude. When a larger impulse is detected, and a faster ball is anticipated, the cue can be advanced. Therefore, the cue's timing for the n-th exchange with respect to the adversary return/ball strike time $t_r(n)$, and the cue's temporal modulation is given as:

$$t_{cue}(n) = t_r(n) + \tau_{total} + \tau_{mod}(n) \quad (17)$$

where $\tau_{mod}(n)$ is the delay used to encode the cueing signal, which is given as $$\tau_{mod}(n) = \tau_{nom} + \tau_{cue}(n) \quad (18)$$

where $\tau_{nom}$ is the nominal positive delay used to enable a cue advance and $\tau_{cue}(n)$ is the varying time shift which encodes the cue signal based on impulse magnitude with respect to a nominal impulse magnitude:

$$\tau_{cue}(n) = k I_r(n) \quad (19)$$

Where k is a scale factor. The nominal shift could be based on statistics over the past N exchanges for example $$\tau_{nom}(n) = k \bar{I}_r(n) \quad (20)$$

where $\bar{I}_r(n)$ represents the average impulse over the past N exchanges at instant n.

Without this nominal delay advancing the cue is not possible. The nominal delay can be calibrated based on the player's performance.

Amplitude modulation. The other form of encoding for the cueing is modulation of the stimuli's amplitude (i.e. volume). For example, the magnitude of the measured racket impulse can be used to increase or decrease the cue amplitude w.r.t. a nominal strength. The duration and strength of stimulus has a significant effect on reaction time. Luce, Response Times: Their Role in Inferring Elementary Mental Organization, Oxford University Press (1986). Therefore, the stimulus strength can be modulated to achieve the desired cueing effect.

Frequency modulation. The cues stimuli can also be modulated in their frequency, i.e. changing the pitch or tone of the stimuli. For example, a higher pitch cue stimulus can be used for larger stroke speed to help anticipate a faster oncoming ball.

Cue Signal Communication

The cueing signal can be communicated to the player through various forms of stimuli, including visual, auditory and/or haptic mechanisms.

The auditory signaling has the advantage that it can be modulated and also has a low physiological latency. Furthermore, the auditory system is already involved in extracting cues in natural playing conditions.

Another suitable mechanism for communication of cue signal is haptic. This modality has the advantage that it could be blended with the user's proprioceptive and motor control processes. Haptic signaling can for example be achieved using a piezoelectric transducer embedded in the racket frame or directly in the grip or handle. When embedded in the racket handle the transducers can be arranged in an array or map to provide intuitive cueing stimuli. For example, a cue to signal the need for a slice could be communicated by a pattern of tactile stimuli that is correlated with the grip force interactions experienced during a slice.

Immersive visual devices such as the Google glasses or Microsoft HoloLens provide opportunities to overlay cue signals to the visual field. Holograms are particularly attractive since they enable mixed reality that blend the actual physical environment (e.g. the tennis court) with holographic elements. This capability can be used to augment the participant's perceived environment and the perception of the other actor's behavior. In tennis, elements that can be overlaid include: a vector that represents the direction and magnitude of the shot leaving the adversary's racket; indicating the expected bounce location of the ball; and/or highlighting the optimal impact zone for the stroke.

Gaze tracking systems can also be used to obtain participants perceptual states such as their visual attention. This information can then be used interactively with the cueing system. This is in particular relevant when using visual cueing.

The systems and methods according to aspects of the disclosed subject matter may also utilize a variety of computer and computing systems, communications devices, networks and/or digital/logic devices for operation. Each may, in turn, be configurable to utilize a suitable computing device that can be manufactured with, loaded with and/or fetch from some storage device, and then execute, instructions that cause the computing device to perform a method according to aspects of the disclosed subject matter.

A computing device can include without limitation a mobile user device such as a mobile phone, a smart phone and a cellular phone, a personal digital assistant ("PDA"), such as a BLACKBERRY, IPHONE, a tablet, a laptop and the like. In at least some configurations, a user can execute a browser application over a network, such as the Internet, to view and interact with digital content, such as screen displays. A display includes, for example, an interface that allows a visual presentation of data from a computing device. Access could be over or partially over other forms of computing and/or communications networks. A user may access a web browser, e.g., to provide access to applications and data and other content located on a website or a webpage of a web site.

A suitable computing device may include a processor to perform logic and other computing operations, e.g., a stand-alone computer processing unit ("CPU"), or hard wired logic as in a microcontroller, or a combination of both, and may execute instructions according to its operating system and the instructions to perform the steps of the method, or elements of the process. The user's computing device may be part of a network of computing devices and the methods of the disclosed subject matter may be performed by different computing devices associated with the network, perhaps in different physical locations, cooperating or otherwise interacting to perform a disclosed method. For example, a user's portable computing device may run an app alone or in conjunction with a remote computing device, such as a server on the Internet. For purposes of the present application, the term "computing device" includes any and all of the above discussed logic circuitry, communications devices and digital processing capabilities or combinations of these.

Certain embodiments of the disclosed subject matter may be described for illustrative purposes as steps of a method that may be executed on a computing device executing software, and illustrated, by way of example only, as a block diagram of a process flow. Such may also be considered as a software flow chart. Such block diagrams and like operational illustrations of a method performed or the operation of a computing device and any combination of blocks in a block diagram, can illustrate, as examples, software program code/instructions that can be provided to the computing device or at least abbreviated statements of the functionalities and operations performed by the computing device in executing the instructions. Some possible alternate implementation may involve the function, functionalities and operations noted in the blocks of a block diagram occurring out of the order noted in the block diagram, including occurring simultaneously or nearly so, or in another order or not occurring at all. Aspects of the disclosed subject matter may be implemented in parallel or seriatim in hardware, firmware, software or any combination(s) of these, co-located or remotely located, at least in part, from each other, e.g., in arrays or networks of computing devices, over interconnected networks, including the Internet, and the like.

The instructions may be stored on a suitable "machine readable medium" within a computing device or in communication with or otherwise accessible to the computing device. As used in the present application a machine readable medium is a tangible storage device and the instructions are stored in a non-transitory way. At the same time, during operation, the instructions may at some times be transitory, e.g., in transit from a remote storage device to a computing device over a communication link. However, when the machine readable medium is tangible and non-transitory, the instructions will be stored, for at least some period of time, in a memory storage device, such as a random access memory (RAM), read only memory (ROM), a magnetic or optical disc storage device, or the like, arrays and/or combinations of which may form a local cache memory, e.g., residing on a processor integrated circuit, a local main memory, e.g., housed within an enclosure for a processor of a computing device, a local electronic or disc hard drive, a remote storage location connected to a local server or a remote server access over a network, or the like. When so stored, the software will constitute a "machine readable medium," that is both tangible and stores the instructions in a non-transitory form. At a minimum, therefore, the machine readable medium storing instructions for execution on an associated computing device will be "tangible" and "non-transitory" at the time of execution of instructions by a processor of a computing device and when the instructions are being stored for subsequent access by a computing device.

Additionally, a communication system of the disclosure comprises: a sensor as disclosed; a server computer system; a measurement module on the server computer system for permitting the transmission of a measurement from a detection device over a network; at least one of an API (application program interface) engine connected to at least one of the detection device to create a message about the measurement and transmit the message over an API integrated network to a recipient having a predetermined recipient user name, an SMS (short message service) engine connected to at least one of the system for detecting physiological parameters and the detection device to create an SMS message about the measurement and transmit the SMS message over a network to a recipient device having a predetermined measurement recipient telephone number, and an email engine connected to at least one of the detection device to create an email message about the measurement and transmit the email message over the network to a recipient email having a predetermined recipient email address.

Communications capabilities also include the capability to communicate and display relevant performance information to the user, and support both ANT+ and Bluetooth Smart wireless communications. A storing module on the server computer system for storing the measurement in a detection device server database can also be provided. In some system configurations, the detection device is connectable to the server computer system over at least one of a mobile phone network and an Internet network, and a browser on the measurement recipient electronic device is used to retrieve an interface on the server computer system. In still other configurations, the system further comprising: an interface on the server computer system, the interface being retrievable by an application on the mobile device. Additionally, the server computer system can be configured such that it is connectable over a cellular phone network to receive a response from the measurement recipient mobile device.

The system can further comprise: a downloadable application residing on the measurement recipient mobile device, the downloadable application transmitting the response and a measurement recipient phone number ID over the cellular phone network to the server computer system, the server computer system utilizing the measurement recipient phone number ID to associate the response with the SMS measurement. Additionally, the system can be configured to comprise: a transmissions module that transmits the measurement over a network other than the cellular phone SMS network to a measurement recipient user computer system, in parallel with the measurement that is sent over the cellular phone SMS network.

Different architectures can be used for the communication between cueing devices, the cue administration and use of a host computer for processing. The general categories of topologies are distributed or centralized architectures. For example, in a basic distributed architecture cueing devices integrate the processing, sensing, and cue administrator. The devices can then communicate through a local network, local cloud or internet. For added flexibility, the cue administrator may be a separate system or unit in communication with the cueing device. For example, miniature Bluetooth speakers could be used to administer the cue. Alternatively, eye glasses such as the Microsoft HoloLense. This system can be scaled to more than two participants. In this case it may be more efficient to include a central processing unit such as a host computer. This system could then receive and process the information from the various cueing devices as well as more global data from the environment such as obtained from a motion capture system (HAWK-EYE, VICON, etc.). The combined data can then be used to run large scale interaction models that can determine cues to coordinate multiple participants considering the larger task objectives.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A cueing device comprising:
    one or more sensors configured to take measurement data for one or more participants engaged in an activity in an environment;
    a processor in communication with the one or more sensors, the processor configured to:
    analyze the measurement data from the one or more sensors to detect events associated with the environment and the one or more participants;
    extract attributes associated with the events from the measurement data;
    predict a movement outcome associated with one of the events, based on the extracted attributes; and
    generate one or more instructions based on the predicted movement outcome;
    a cue administrator configured to generate one or more anticipatory cues for the one or more participants based on the one or more instructions generated from the processor, wherein the one or more anticipatory cues are administered as cue stimuli encoding timing and magnitude information selected to reduce a response time between the one event and recognition of the one event by the one or more participants; and
    a wireless transmitter in communication with a user device configured for access to the measurement data collected during the activity.

2. The cueing device of claim 1, wherein the one or more anticipatory cues are selected to enhance situational awareness of the one or more participants, to enhance attention to the event and relevant aspects of behavior of the one or more participants, or to provide temporal cue stimuli following said event comprising stroke preparation or stroke initiation.

3. The cueing device of claim 1, wherein the one or more anticipatory cues are administered with a nominal delay that varies based on the magnitude information.

4. The cueing device of claim 1, wherein the anticipatory cues are based on a combination of signals from first and second participants of the one or more participants, and wherein a phase difference between the signals provides a measure of advance or delay used to modulate the cues.

5. The cueing device of claim 1, wherein the one or more anticipatory cues comprise a rhythmic pattern of signals selected from auditory, visual, and haptic signals, and wherein the rhythmic pattern is adjusted based on a desired pace of performance of the activity by the one or more participants.

6. The cueing device of claim 1, wherein the processor is further configured to estimate state data for each of the participants and for the environment based on the measurement data from the one or more sensors, wherein the state data for the participants and the environment are combined to determine the predicted movement outcomes.

7. The cueing device of claim 6, wherein the wireless transmitter is configured to communicate a portion of the state data to a user device of a coach, and wherein the cue administrator provides real-time input from the user device of the coach to the one or more participants.

8. The cueing device of claim 6, wherein the activity comprise a procedure and the state data for the participants describe team member states for team members engaged in a stage of the procedure.

9. The cueing device of claim 1, wherein the cueing device is wearable and the cue administrator comprises one or more of a speaker, a light emitter, or a vibration generator.

10. A method of operating the cueing device of claim 1, the method comprising the wireless transmitter communicating with the user device comprising a mobile phone, smart phone, personal digital assistant, laptop or tablet computer for access to the measurement data collected during the activity.

11. A cueing system comprising:
a first cueing device having one or more sensors configured in communication with a first processor to collect data for a first participant engaged in an activity, wherein the first processor is configured to analyze the data to detect first events associated with the first participant, to extract attributes associated with the first events, to predict movement outcomes associated with the first events based on the extracted attributes, and to generate one or more first instructions based thereon, and
a first cue administrator in communication with the first processor to generate one or more anticipatory cues based on the first instructions; and
a second cueing device in wireless communication with the first cueing device and having one or more second sensors configured in communication with a second cueing processor to collect data for a second participant engaged in the activity, wherein the second processor is configured to analyze the data to detect second events associated with the second participant, to extract attributes associated with the events, to predict movement outcomes associated with the second events based on the extracted attributes, and to generate one or more second instructions based thereon, and
a second cue administrator in communication with the second processor to generate one or more anticipatory cues based on the second instructions;
wherein the one or more anticipatory cues are administered as cue stimuli encoding timing and magnitude information selected to reduce a response time between the first and second events and recognition of the first and second events by the participants.

12. The cueing system of claim 11, wherein the one or more anticipatory cues are selected to enhance situational awareness of the first and second participants, or to enhance attention to the first and second events and relevant aspects of behavior of the first and second participants.

13. The cueing system of claim 11, wherein the one or more anticipatory cues are administered with a nominal delay that varies based on the magnitude information, or based on a combination of signals from the first and second participants, wherein a phase difference between the signals provides a measure of the delay.

14. The cueing system of claim 13, wherein the activity in which the participants are engaged is cooperative and the delay is calibrated based on performance of the participants in the activity.

15. The cueing system of claim 11, wherein the first and second processors are further configured to estimate state data for each of the respective participants and for the environment based on the data from the respective sensors, wherein the state data for the participants and the environment are combined to predict the movement outcomes.

16. The cueing system of claim 15, wherein the activity comprises a procedure and the state data describe team member states for team members engaged in a stage of the procedure.

17. The cueing system of claim 11, further comprising a vision or optical-based tracking system configured to provide ball location or trajectory data for the first and second events relative to a court, wherein the ball location or trajectory data are processed to extract event data including net crossing, ground impact or racket impact data.

18. The cueing system of claim 17, wherein the ball location or trajectory data are further processed to predict a ball trajectory relative to a court, based on position data from the first and second cueing devices.

19. A method of operating the cueing system of claim 11, the method comprising wireless communication with a user device configured for access to the data collected during the activity, wherein the cue administrators provides real-time input from the user device.

20. A system for cueing in an environment, the system comprising:
a cueing device having one or more sensors selected to obtain sensed data taken for one or more participants engaged in an activity in an environment;
a processor in communication with the one or more sensors, the processor configured for:
analyzing the obtained data to detect an event associated with the one or more participants;
extracting attributes associated with the event from the obtained data;
predicting a movement outcome associated with the event in the environment based on the attributes extracted from the analyzed data; and
generating an instruction to issue an anticipatory cue based on the predicted movement outcome; and
a transmitter configured for communicating the anticipatory cue to one or more of the participants, wherein the anticipatory cue is administered as a cue stimulus encoding timing and magnitude information selected to reduce a response time between the event and recognition of the event by the one or more participants.

21. The system of claim 20, wherein the anticipatory cue is administered with a nominal delay that varies based on the magnitude information, or based on a combination of signals from a first and a second of said participants, wherein a phase difference between the signals provides a measure of the delay.

22. The system of claim 20, wherein the processor is further configured to estimate state data for each of the participants and for the environment based on the sensed data, wherein the state data for the participants and the environment are combined to predict the movement outcomes.

23. The system of claim 22, wherein the activity comprise a procedure and the state data for the participants describe team member states for team members cooperatively engaged in a stage of the procedure.

24. A method of operating the system of claim 20, the method comprising the transmitter wirelessly communicating with tablet user device for access to the sensed data obtained during the activity, wherein the cue stimulus further provides real-time input from the user device.

* * * * *